US011559253B2

(12) United States Patent
Mattis et al.

(10) Patent No.: US 11,559,253 B2
(45) Date of Patent: Jan. 24, 2023

(54) WEARABLE PHYSICAL-ACTIVITY MEASUREMENT SYSTEM FOR BALANCING PHYSICAL-ACTIVITY ENERGY EXPENDITURE AND BASAL METABOLIC RATE TO FOOD ENERGY INTAKE BY ADJUSTING MEASURED PORTIONS OF FOOD INGREDIENTS

(71) Applicant: World Champ Tech, LLC, Mountain View, CA (US)

(72) Inventors: James Alexander Mattis, Mountain View, CA (US); Troy Anthony Porter, San Jose, CA (US); John Novitsky, Woodside, CA (US)

(*) Notice: Subject to any disclaimer, the term of this patent is extended or adjusted under 35 U.S.C. 154(b) by 1070 days.

(21) Appl. No.: 16/146,493

(22) Filed: Sep. 28, 2018

(65) Prior Publication Data

US 2019/0099124 A1    Apr. 4, 2019

Related U.S. Application Data

(60) Provisional application No. 62/565,749, filed on Sep. 29, 2017.

(51) Int. Cl.
*A61B 5/00* (2006.01)
*A61B 5/11* (2006.01)
(Continued)

(52) U.S. Cl.
CPC ............ *A61B 5/486* (2013.01); *A61B 5/0022* (2013.01); *A61B 5/0205* (2013.01);
(Continued)

(58) Field of Classification Search
CPC ......... A61B 5/024; A61B 5/083; A61B 5/222; A61B 5/375; A61B 5/486; A61B 5/742;
(Continued)

(56) References Cited

U.S. PATENT DOCUMENTS 4,686,624 A    8/1987  Blum et al.
4,797,818 A    1/1989  Cotter
(Continued)

FOREIGN PATENT DOCUMENTS

CN    106200531 A    12/2016
CN    205787762 U    12/2016
(Continued)

*Primary Examiner* — Jay Trent Liddle
*Assistant Examiner* — Alyssa N Brandley
(74) *Attorney, Agent, or Firm* — CrossPond Law

(57) ABSTRACT

An energy balancing system scales portion sizes of user-selected meal recipes to control a digital scale to prompt the user to measure scaled quantities of meal ingredients to prepare scaled meals. Physical activity tracking devices provide data to generate physical activity energy expenditures for energy burned by physical activity. The physical activity energy is added to a basal metabolic rate of energy expenditure that is a function of sex, weight, height, and age. The total energy expended are scaled down for a weight-loss goal to obtain the total recommended energy. A recipe portion-size optimizer adjusts scaling factors for each recipe so that the total recommended energy is met by the scaled meals. Amounts of nutrients for the recipes can also be scaled by the scaling factors to match recommended nutrient amounts when the meal recipe optimizer generates the scaling factors using an over-determined linear system optimizer.

15 Claims, 14 Drawing Sheets

(51) Int. Cl.

| | | |
|---|---|---|
| *A61B 5/0205* | (2006.01) | |
| *G16H 20/30* | (2018.01) | |
| *G16H 20/60* | (2018.01) | |
| *G09B 19/00* | (2006.01) | |
| *A61B 5/024* | (2006.01) | |
| *A61B 5/083* | (2006.01) | |
| *A61B 5/145* | (2006.01) | |
| *A61B 5/22* | (2006.01) | |

(52) U.S. Cl.
CPC ......... *A61B 5/1112* (2013.01); *A61B 5/1118* (2013.01); *A61B 5/4866* (2013.01); *G09B 19/0092* (2013.01); *G16H 20/30* (2018.01); *G16H 20/60* (2018.01); *A61B 5/024* (2013.01); *A61B 5/083* (2013.01); *A61B 5/1121* (2013.01); *A61B 5/14546* (2013.01); *A61B 5/224* (2013.01); *A61B 2560/0431* (2013.01); *A61B 2562/0219* (2013.01)

(58) Field of Classification Search
CPC ... A61B 5/0022; A61B 5/0205; A61B 5/1112; A61B 5/1118; A61B 5/1121; A61B 5/4866; A61B 5/6824; A61B 5/6831; A61B 2560/0431; A61B 2562/0219; A61B 5/2505; G16H 20/30; G16H 20/60; G16H 40/67; G09B 19/00; G09B 19/0092; G09B 5/125; A63B 24/0062; A63B 2230/75; G06F 15/025; G06Q 50/12; G01G 19/00; G01G 19/4146
USPC ....................................................... 434/127
See application file for complete search history.

(56) References Cited

U.S. PATENT DOCUMENTS

| | | | |
|---|---|---|---|
| 5,673,691 A | 10/1997 | Abrams et al. | |
| 5,954,640 A | 9/1999 | Szabo | |
| 6,283,914 B1 | 9/2001 | Mansfield et al. | |
| 6,370,513 B1 | 4/2002 | Kolawa et al. | |
| 6,478,736 B1 | 11/2002 | Mault | |
| 6,513,532 B2 | 2/2003 | Mault et al. | |
| 6,878,885 B2 | 4/2005 | Miller-Kovach et al. | |
| 7,361,143 B2 | 4/2008 | Kirchhoff et al. | |
| 7,523,040 B2 | 4/2009 | Kirchhoff et al. | |
| 8,690,578 B1 | 4/2014 | Nusbaum et al. | |
| 8,829,365 B1* | 9/2014 | Wallace | G01G 19/56 177/25.14 |
| 2002/0133378 A1* | 9/2002 | Mault | G16H 20/60 705/3 |
| 2003/0091964 A1* | 5/2003 | Yeager | G16H 70/00 708/133 |
| 2003/0208110 A1* | 11/2003 | Mault | A61B 5/0833 600/300 |
| 2010/0228160 A1* | 9/2010 | Schweizer | G16H 20/60 600/595 |
| 2011/0151414 A1 | 6/2011 | McCarthy et al. | |
| 2012/0083669 A1* | 4/2012 | Abujbara | G16H 20/60 600/300 |
| 2014/0255882 A1* | 9/2014 | Hadad | G09B 19/0092 434/127 |
| 2015/0093725 A1* | 4/2015 | Baarman | G09B 5/00 600/300 |
| 2015/0279235 A1* | 10/2015 | Yamada | G06Q 50/10 434/127 |
| 2015/0305564 A1* | 10/2015 | Jimenez | A47J 36/321 366/141 |
| 2016/0166195 A1* | 6/2016 | Radecka | A61B 5/112 600/595 |
| 2016/0328669 A1 | 11/2016 | Droege | |
| 2017/0061518 A1 | 3/2017 | Cao | |
| 2017/0091880 A1 | 3/2017 | Krishnan et al. | |
| 2017/0116879 A1* | 4/2017 | Baarman | A61B 5/024 |

FOREIGN PATENT DOCUMENTS

| | | |
|---|---|---|
| CN | 106295989 A | 1/2017 |
| CN | 106355317 A | 1/2017 |
| CN | 106355364 A | 1/2017 |
| EP | 3105151 A1 | 12/2016 |
| KR | 20160110814 A | 9/2016 |
| WO | WO2015118182 A | 8/2015 |
| WO | WO2016162546 A1 | 10/2016 |
| WO | WO2016162546 A8 | 11/2016 |
| WO | WO2016176464 A1 | 11/2016 |
| WO | WO2016198964 A1 | 12/2016 |
| WO | WO2017012100 A1 | 1/2017 |
| WO | WO2017012101 A1 | 1/2017 |
| WO | WO2017019501 A1 | 2/2017 |

\* cited by examiner

WEARABLE PHYSICAL-ACTIVITY MEASUREMENT SYSTEM FOR BALANCING PHYSICAL-ACTIVITY ENERGY EXPENDITURE AND BASAL METABOLIC RATE TO FOOD ENERGY INTAKE BY ADJUSTING MEASURED PORTIONS OF FOOD INGREDIENTS

RELATED APPLICATION

This application claims the benefit of priority to provisional application U.S. Ser. No. 62/565,749, filed Sep. 29, 2017, which is hereby incorporated by reference.

FIELD OF THE INVENTION

This invention relates to diet and physical activity monitoring devices, and more particularly to balancing measured activity and basal needs with consumption by scaling measured recipe portion sizes.

BACKGROUND OF THE INVENTION

Weight gain or loss of a human subject is ultimately determined by the first law of thermodynamics: energy input minus energy output equals energy storage, or more succinctly, in minus out equals accumulation. To maintain weight, energy input, such as from the energy of food ingested, must match the energy expended by the human body.

In the United States, food energy intake typically is expressed in units of calories, which is shorthand for kilocalories (Kcals). In the metric system, the units for food energy intake are kilojoules, which are used throughout the description of the invention. Kilocalories may be converted to kilojoules through a constant conversion factor and vice versa.

FIG. 1 is a graph showing how net energy causes weight gain or loss. The x axis shows the net energy per day, which is the total intake of food, expressed in kilojoules (kJ) of energy, minus the energy expended by the human body for that day. When the person eats exactly the same amount of energy of food as the energy burned that day, the net energy per day is zero, and the weight gain is zero. However, if the person eats 4000 kilojoules per day more that their body needs, that person can be expected to gain about 1 kilogram per week.

Alternately, if a person reduces their food intake, or increases physical activity so that the person is burning 4000 kilojoules per day more than consuming, that person can be expected to lose 1 kilogram each week. Line 150 is a graphical expression of the first law of thermodynamics, showing weight gain or loss as a function of energy imbalances.

FIG. 2 is a graph depicting the effects of physical activity and energy intake on weight change. A perfect balance occurs when the energy consumed, curve 152, exactly match the energy expended, curve 154. Curve 154 includes all energy expended by the human body over a 24-hour period, which includes physical activity and rest periods.

When the person increases consumption, but maintains the same physical activity and resting energy expenditure, the energy consumed per day increases along curve 152, causing a positive net energy per day and a weight gain. If the person instead were to reduce food consumption, the net energy would decrease along curve 152, resulting in a weight loss.

When food consumption is maintained at the balance point, but energy expenditure is increased, such as by increased physical activity, the energy expended per day increases along curve 154 to the right of the (0,0) balance point, resulting in a weight loss. Alternatively, reducing physical activity causes a weigh gain as shown by the portion of curve 154 to the left of the (0,0) balance point.

Higher energy consumption causes weight gain while higher energy expenditure due to physical activity causes weight loss, as can be seen with curve 152 having a positive slope but curve 154 having a negative slope.

The energy expenditure by a human body is quite complex. FIG. 3 shows the energy expenditure of a human body over a 24-hour day. The energy burned per hour is low during sleep and has peaks and valleys throughout the day. Peak 158 could be caused by exercise, such as by a morning run, while trough 156 could be caused by inactivity during a dull office meeting.

Activity trackers, such as smart phones, smart watches, and other wearables, are useful for monitoring physical activity. Position data or movement data, such as obtained by Global Positioning System (GPS), accelerometers, and gyroscopes can be used to estimate the energy burned by physical activity, perhaps in combination with other data such as a user's weight or age. Some wearables can measure heart rate, allowing for estimates of energy expenditure for both physical activity and rest periods. While useful for estimating energy burned by physical activity, these devices don't measure the actual food energy consumed per day so these devices can perform only half of the energy balance.

Digital scales are also available to accurately measure foods. Some digital scales can be combined with food databases and user input to calculate energy for food items. Diet plans typically have recipes with fixed amounts of ingredients, and fixed portion sizes that are not adjusted for an individual's exact daily needs. Some diet plans have pre-packaged meals with set energy measures, but they don't scale portions up or down depending on that day's energy needs, or only superficially adjust meal plans, such as by giving a bonus dessert or energy bar. Ultimately the person on the plan needs to measure their weight and cut back further when the weight goes up instead of down. While useful for measuring energy consumed by the user, digital scales also can only perform half of the energy balance.

Because an individual's actual energy expenditure may vary significantly from day to day, following a standard diet is likely to result in days of weight gain and other days of weight loss. These weight fluctuations, termed weight cycling or yo-yo dieting, can discourage an individual, and impede progress towards goals. It would be better to eat the exact amount of energy needed each day to avoid daily fluctuations in weight due to these daily imbalances. Steady progress likely would minimize the anxiety and frustration an individual experiences as a result of yo-yo dieting.

Additionally, as an individual changes their diet to gain or lose weight by adjusting their dietary energy intake, the quantities of other nutrients the individual consumes, including vitamins, minerals, essential fatty acids, water, and essential amino acids will also change.

It would be desirable to accurately estimate the energy expenditure for a whole 24-hour period, including both periods of physical activity and periods of rest, sleep, and other normal activities. It is desirable to use existing fitness-tracking devices to measure energy expenditure during physical activity periods and rest periods. It would further be desirable to measure and adjust meal portions to exactly match the actual energy expenditure and additionally ensure that dietary nutrient targets are met. It is desirable to integrate data from activity trackers, digital food scales, and resting energy needs to perform an energy balance each day for an individual human user, rather than use pre-set meal portions.

What is desired is an integrated physical activity and diet monitor. A system that accounts for both physical activity and basal metabolic energy expenditure, and then adjusts meals to exactly match the measured or estimated energy expenditure is desired. An individualized portion adjuster based on that individual's actual daily energy needs is desirable. It is desirable that the diet monitor system prescribes a diet that also meets all nutrient requirements and needs.

DETAILED DESCRIPTION

The present invention relates to an improvement in weight-management and weight-loss systems. The following description is presented to enable one of ordinary skill in the art to make and use the invention as provided in the context of a particular application and its requirements. Various modifications to the preferred embodiment will be apparent to those with skill in the art, and the general principles defined herein may be applied to other embodiments. Therefore, the present invention is not intended to be limited to the particular embodiments shown and described, but is to be accorded the widest scope consistent with the principles and novel features herein disclosed.

Figure 4:
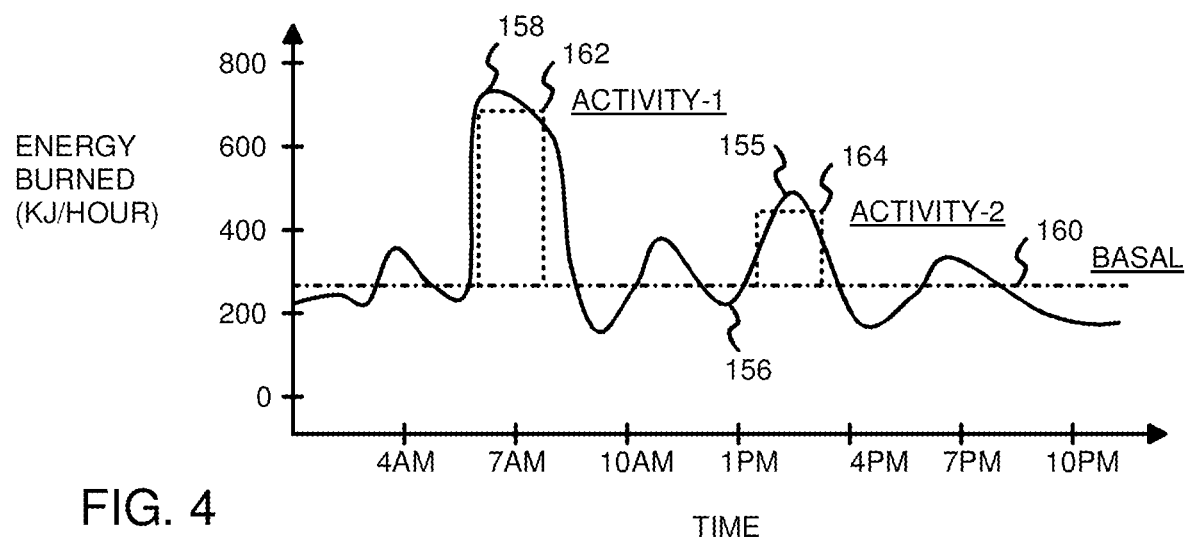
FIG. 4 is a graph showing basal and physical activity energy expenditure.

FIG. 4 is a graph showing basal and physical activity energy expenditure. While the user's energy expenditure varies throughout the day, as shown by energy expenditure curve 155 with peak 158 and trough 156, the inventors realize that energy expenditure curve 155 can be modeled as a constant basal or resting rate that remains the same throughout the day, and periods of physical activity.

In FIG. 4, energy expenditure curve 155 is modeled as basal rate 160, which remains constant for all 24 hours of the day, and physical activities 162, 164. Peak 158 is caused by an exercise activity, such as a morning run. The energy expenditure of this activity can be measured by a fitness-tracking device such as a smartwatch, producing an energy total for physical activity 162, which is added to basal rate 160.

Likewise, the total energy expended by physical activity 164 can be measured by a wearable tracking device and added to basal rate 160. The total energy expended during the 24 hour day is then basal rate 160 over the 24 hours, plus the total energy for physical activities 162, 164.

The inventors realize that the resting or basal energy expenditure varies significantly from one person to another. However, basal rate 160 can be modeled with a formula that has a few significant factors. Significant factors include the person's sex, weight, height, and age. The person's body fat percentage may also be a factor in more advanced models, such as statistical regression models.

The inventors model energy expenditure curve 155 as basal rate 160, estimated by the models using the significant factors or sex, weight, height, and age, plus the added energy determined from fitness-tracking devices that measure physical activities 162, 164.

Figure 5:
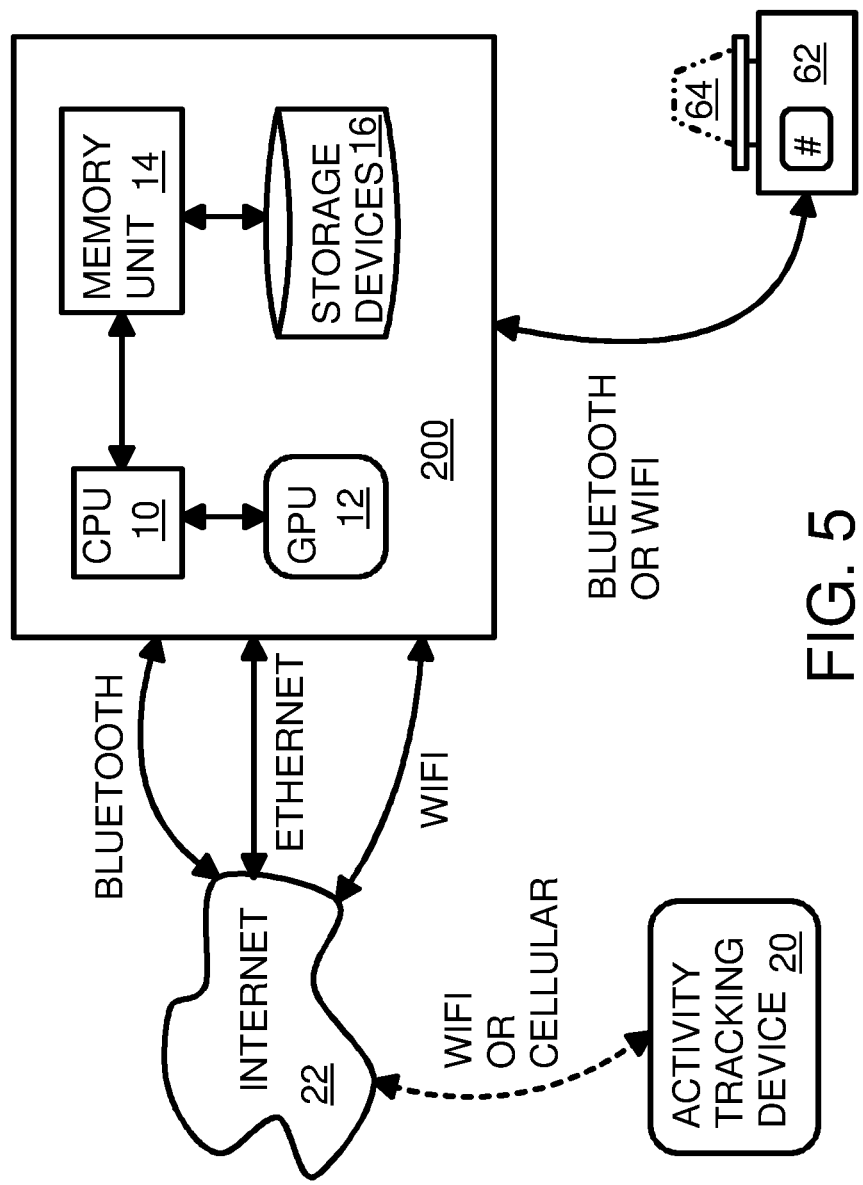
FIG. 5 shows a server-based computing system that reads energy expenditure from a fitness-tracking device and measures food with a digital scale.

FIG. 5 shows a server-based computing system that reads energy expenditure from a fitness-tracking device and measures food with a digital scale. Server 200 uses Central Processing Unit (CPU) 10 to execute programs of instructions that are stored in memory unit 14 and operate on data that is backed up in storage devices 16.

Graphics Processing Units (GPU) 12 generates graphics data for display to a user. The inventors also realize that GPU are especially efficient at performing matrix operations, such as used by the energy balancing system described in detail later.

Server 200 communicates with activity tracking device 20 through Internet 22. A wireless connection, utilizing a protocol such as the WI-FI® protocol of the Wi-Fi Alliance of Austin, Tex., utilizing a cellular data network, or other wireless connection, can be made from activity tracking device 20 to Internet 22, while a wired Ethernet connection may be made from Internet 22 to server 200. A different wireless connection, utilizing a protocol such as the BLUETOOTH® protocol of the Bluetooth SIG of Kirkland, Wash. or may also be used to connect to server 200, especially for smaller servers.

Server 200 also connects through Internet 22 to digital scale 62 over a wireless connection, utilizing a protocol such as the WI-FI® protocol of the Wi-Fi Alliance of Austin, Tex. or the BLUETOOTH® protocol of the Bluetooth SIG of Kirkland, Wash., utilizing a cellular data network, or other wireless connection, perhaps through a local computer or other device such as a smart phone (not shown) that pairs with digital scale 62. Digital scale 62 measures the weight of food 64. The user may be allowed to input a food description into digital scale 62, and a display on digital scale 62 may be used to display messages from server 200 to the user.

An energy balancing program is executed on server 200 and receives activity data from activity tracking device 20 that is converted into energy expenditures for physical activities 162, 164 (FIG. 4) that are added to basal rate 160 that server 200 calculates based on the user's sex, weight, height, and age. The energy balancing program running on server 200 then calculates the total energy expended by the user for that day, and generates meal recipes that have a total energy amount that matches the energy expended. When weight loss is desired, the total energy of the meal recipes is somewhat less than the total energy expended. Server 200 sends the meal recipes to the user, and instructs the user to use digital scale 62 to measure the exact amount of food 64 that is needed for the meal recipes generated. Server 200 can interact with digital scale 62 to prompt the user to weigh specific food items, and to verify that the correct amounts of food 64 were weighed.

Activity tracking device 20 and digital scale 62 are together used by the energy tracking program on server 200 to measure activities and adjust food portions to match actual energy expenditure. An energy balance computation can be performed each day by server 200, ensuring that the individual avoids the cycles of weight gain and loss associated with yo-yo dieting.

The user can also input food items consumed that are not weighted by digital scale 62, such as at a restaurant, allowing the energy balancing program to account for all consumption.

Figure 6:
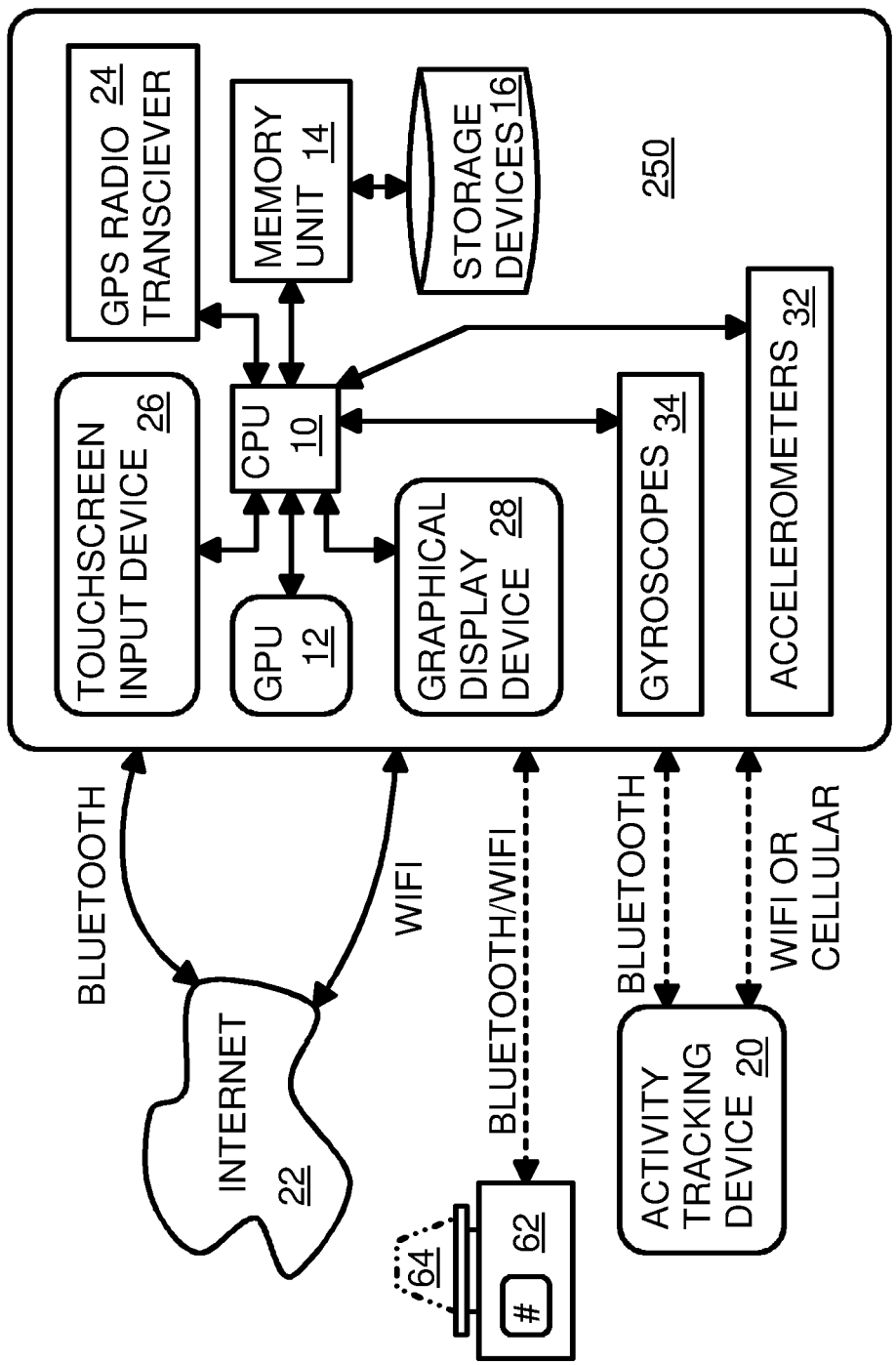
FIG. 6 shows a mobile computing system that reads energy expenditure from a fitness-tracking device and measures food with a digital scale.

FIG. 6 shows a mobile computing system that reads energy expenditure from a fitness-tracking device and measures food with a digital scale. Mobile device 250 can pair directly with activity tracking device 20 using the BLUETOOTH® protocol of the Bluetooth SIG of Kirkland, Wash., or connect to activity tracking device 20 utilizing a protocol such as the WI-FI® protocol of the Wi-Fi Alliance of Austin, Tex. or the BLUETOOTH® protocol of the Bluetooth SIG of Kirkland, Wash., or utilizing a cellular data network. Mobile device 250 also connects to Internet 22 utilizing a protocol such as the WI-FI® protocol of the Wi-Fi Alliance of Austin, Tex. or the BLUETOOTH® protocol of the Bluetooth SIG of Kirkland, Wash., utilizing a cellular data network, or other wireless connection.

Mobile device 250 can display messages and data to the user on graphical display device 28 and use Graphics Processing Unit 12 to format graphical data. The user can make selections, such as for meal preferences, using touch screen input device 26. When activity tracking device 20 is not attached, mobile device 250 can act as an activity tracker using GPS radio transceiver 24 to obtain GPS data that can indicate position data and elevation changes that can be converted to energy expenditures for physical activities 162, 164 (FIG. 4) using an activity-tracking program or using a sub-routine of the energy balancing program.

GPS radio transceiver 24 may be capable of decoding GPS signals into latitude, longitude, and altitude coordinates. The activity-tracking program executing on CPU 10 can also use data from gyroscopes 34 and accelerometers 32 in mobile device 250. Gyroscopes 34 are oriented to measure angular accelerations applied to mobile device 250 in three orthogonal directions, while accelerometers 32 are oriented to measure the accelerations applied to mobile device 250 in three orthogonal directions. Data from accelerometers 32 and gyroscopes 34 can supplement the GPS data, such as to fill in details between GPS data points.

Mobile device 250 can execute instructions stored in memory unit 14 for the energy balancing program and the activity-tracking subroutine, and used data stored in storage devices 16 such as meal recipes and food item energy and nutritional data to control digital scale 62 which can pair with mobile device 250 using a protocol such as the BLUETOOTH® protocol of the Bluetooth SIG of Kirkland, Wash., or be connected through Internet 22. Meal recipe and food item details can be looked up in an external database (not shown) attached to Internet 22 and then cached in storage devices 16.

Figure 7:
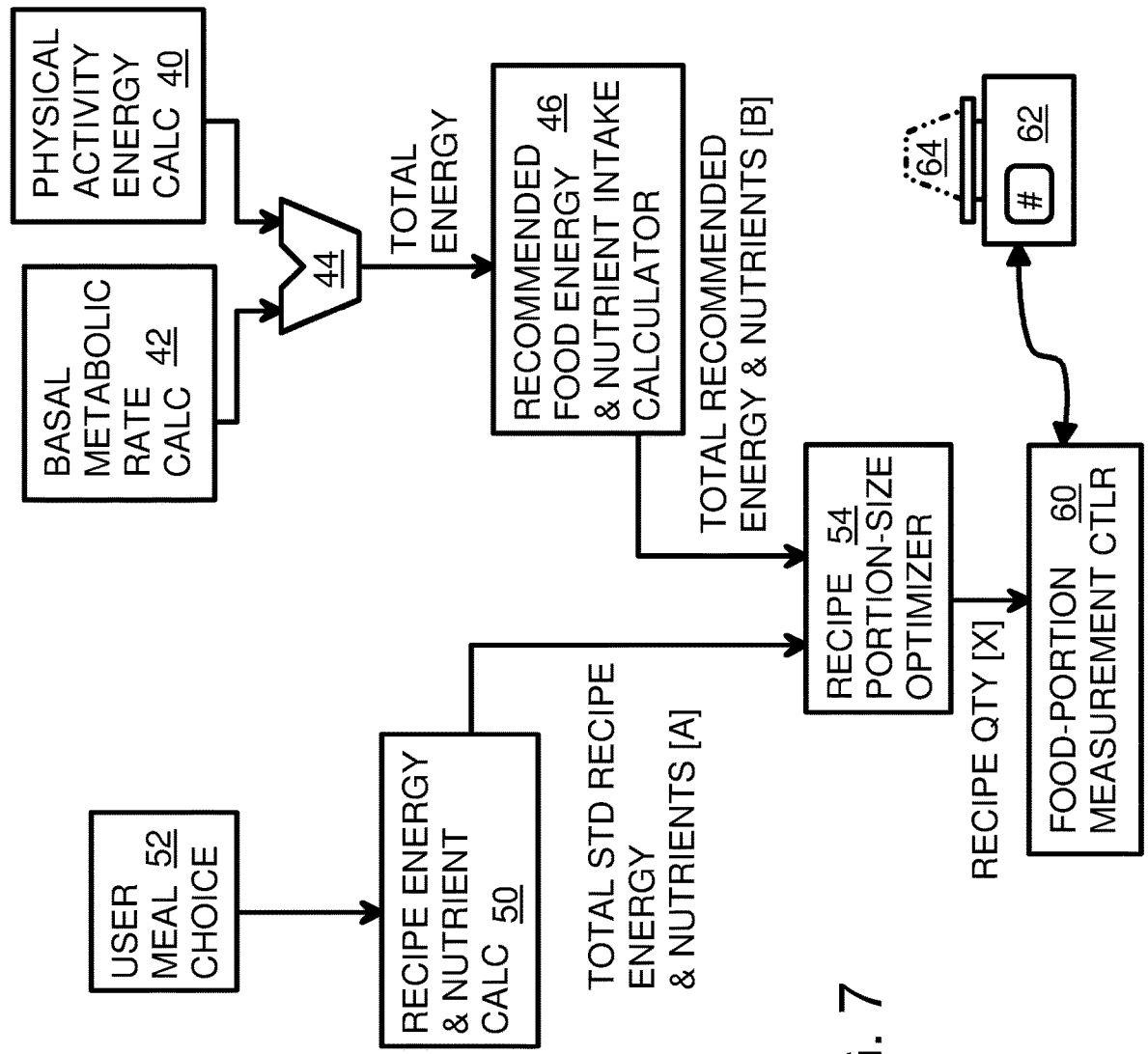
FIG. 7 is a block diagram of an energy balancing system.

FIG. 7 is a block diagram of a energy balancing system. The user inputs data such as their sex, weight, height, and age, or the user's resting metabolic rate is measured, such as in a lab setting. This data is used by basal metabolic rate calculator 42 to generate basal rate 160 (FIG. 4).

Figure 1:
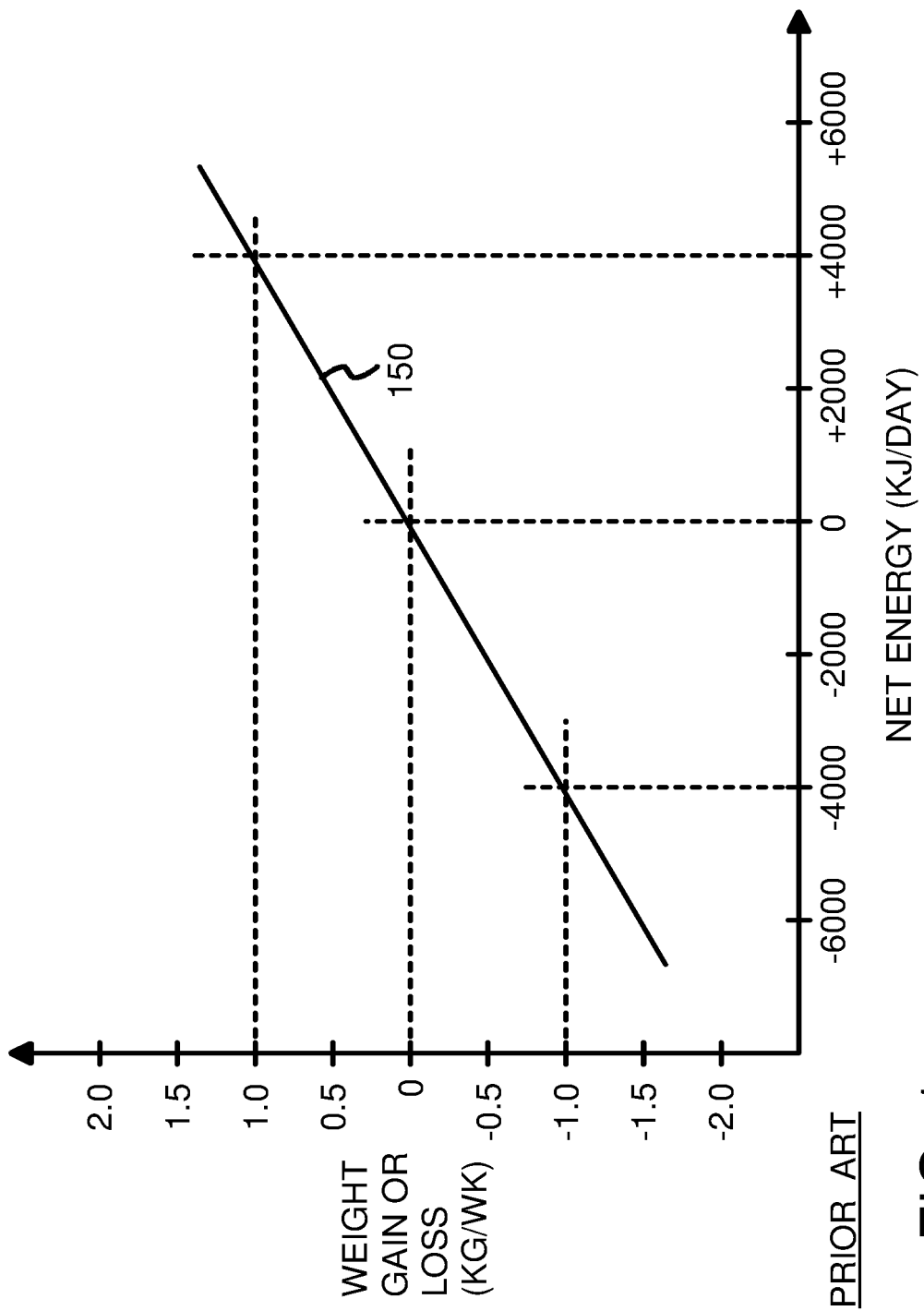
FIG. 1 is a graph showing how net energy causes weight gain or loss.
Figure 2:
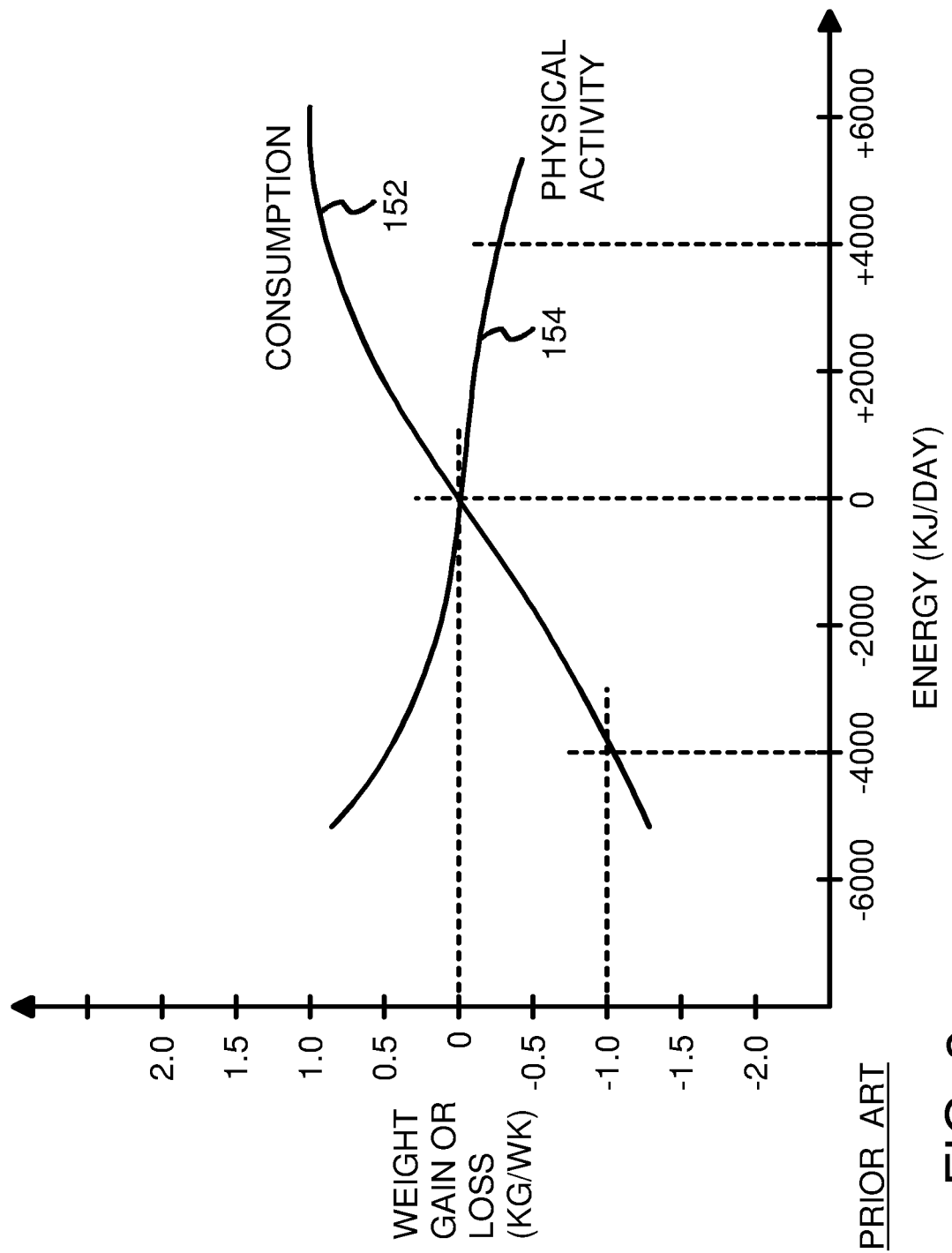
FIG. 2 is a graph depicting the effects of physical activity and energy intake on weight change.
Figure 3:
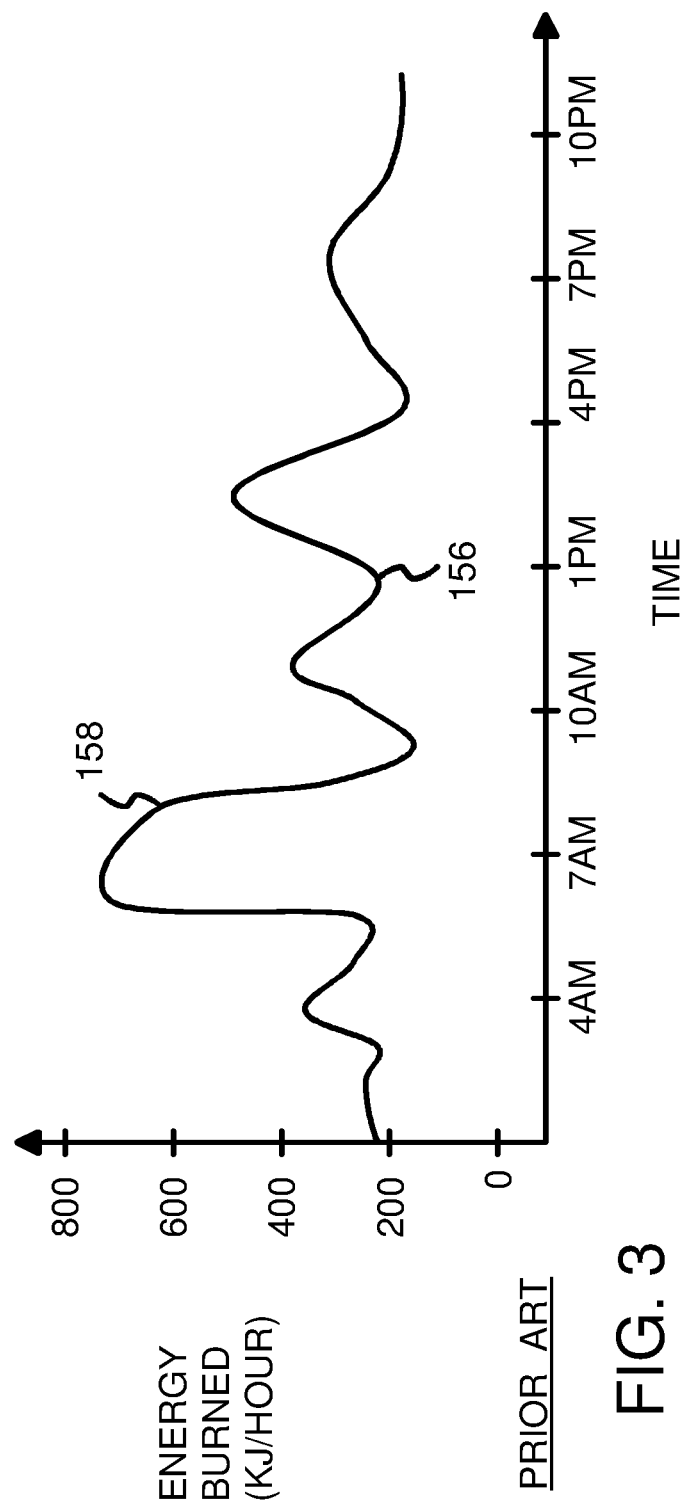
FIG. 3 shows the energy expenditure of a human body over a day.

Physical activities 162, 164 (FIG. 4) are measured by activity tracking device 20 (FIGS. 5, 6) or by an activity-tracking routine on mobile device 250 and the activity data used by physical activity energy calculator 40 to determine energy expenditure by physical activities 162, 164, and any other tracked activities during the day. The energy expenditures of these activities are summed by adder 44 with the basal rate from basal metabolic rate calculator 42 to obtain the total energy (kilojoules) for the day. This total energy is the (0,0) balance point of FIGS. 1, 2 where no net weight gain would occur if this many food kilojoules were consumed.

The total energy generated by adder 44 is input to recommended food energy and nutrient intake calculator 46, which scales the total energy down when weight loss is the goal, or up when weight gain is the user's goal. The amount of scaling can be determined by the user's current weight and target amount of time for a desired amount of weight loss. Medical factors can also be used, such as by limiting the weight change per week to a safe level, even when the user desires faster weight loss or gain.

The recommended energy for the target weight loss or gain can then be divided into macro-nutrients such as protein, carbohydrates, and fat. Target ranges for each macro-nutrient can be determined using diet guidelines or input from a doctor. Targets for other nutrients such as micro-nutrients, vitamins, and minerals can be designated. These nutrient targets can be age or sex adjusted, such as to provide more calcium for older people, provide more iron for females, or provide more sodium on days of heavy physical activity when sodium is lost via sweat. Recommended food energy and nutrient intake calculator 46 outputs a target or recommended energy and nutrient targets to recipe portion-size optimizer 54.

User meal choice interface 52 displays a variety of meal choices or options to the user, such as on the display of mobile device 250, allowing the user to select desired meals. A larger meal database may be accessed to allow the user many choices. Once the user selects one or more meals using user meal choice interface 52, these meal choices are processed by recipe energy and nutrient calculator 50.

Recipe energy and nutrient calculator 50 looks up the meals chosen using user meal choice interface 52 in meal recipe databases to generate a list of ingredients, and energy and nutrient densities for each ingredient. Densities can be expressed as kilojoules per gram of an ingredient, kilojoules per gram, kilojoules per liter, grams of protein per gram of ingredient, etc. The ratios of the various ingredients to each other within a recipe are also generated, or the list of ingredient amounts for a standard portion of the recipe is stored. The amount of an ingredient that is specified in the recipe is multiplied by its energy and nutrient densities to obtain the total standard recipe energy and nutrient amounts.

The standard recipe energy and nutrient amounts generated by recipe energy and nutrient calculator 50 are sent to recipe portion-size optimizer 54. Recipe portion-size optimizer 54 also receives the total recommended energy and nutrients generated by recommended food energy and nutrient intake calculator 46. Recipe portion-size optimizer 54 forms a set of equations for the energy and nutrients. In one of these equations, the recommended energy from recommended food energy and nutrient intake calculator 46 should equal the total energy for the chosen meals that are scaled by the scaled portion size of each meal. Recipe portion-size optimizer 54 finds scaling factors for each of the chosen meals by generating a merit function that indicates how closely the energy of the scaled meals match the recommended energy.

The equation for the energy balance is:

$$E_1 * x_1 + E_2 * x_2 + \ldots + E_n * x_n = RE$$

where RE is the recommended energy, E1 is the energy in a standard portion of food item 1, x1 is the scaling factor for food item 1, etc.

For each nutrient, recipe portion-size optimizer 54 also generates a merit function that indicates how closely that nutrient in the scaled meals matches the target range for that nutrient. Recipe portion-size optimizer 54 can use matrix processing techniques on these equations to find scaling factors that produce minimal error values of the merit functions. Once an acceptable minimum of the merit functions is found by recipe portion-size optimizer 54, the scaling factors for this minimum are generated by recipe portion-size optimizer 54.

The equation for the balance of nutrient Na is:

$$Na_1 * x_1 + Na_2 * x_2 + \ldots + Na_n * x_n = RN_a$$

where RNa is the recommended amount of nutrient Na, Na1 is the amount of nutrient Na in a standard portion of food item 1, x1 is the scaling factor for food item 1, etc. There are multiple nutrient-balance equations for the multiple nutrients.

Rather than solve the equations separately, the energy and nutrient balance equations can be solved simultaneously to determine the optimal set of scaling factor Xn values that both minimizes the difference in energy, and the difference for each nutrient, such as by using least squares to find a minimum of an error or a merit function.

Each scaling factor is multiplied by the standard amount of an ingredient in the base recipe to determine the amount of that ingredient that the user should mix into the meal. An adjusted recipe can be displayed to the user by food-portion measurement controller 60, where each ingredient in the base recipe is scaled by one of the scaling factors that were generated by recipe portion-size optimizer 54. The user can follow the adjusted recipe to make the chosen meal that is scaled in portion size to match the recommended energy intake.

Food-portion measurement controller 60 can control digital scale 62 to measure the calculated amount of each item or ingredient, shown in FIG. 7 as food 64. Digital scale 62 or food-portion measurement controller 60 can indicate to the user which ingredient to measure, and then instruct the user to add more of the ingredient until the weight of that ingredient measured by digital scale 62 matches the calculated amount. The user may be instructed to stop adding more of ingredient when digital scale 62 matches within some tolerance, such as within 5% or 10% of the calculated amount. If the user adds too much of the ingredient, food-portion measurement controller 60 or digital scale 62 can indicate that the user should remove some of the ingredient.

When all the ingredients of food 64 are mixed together and prepared, the user can eat the chosen meals that are scaled to match the recommended energy intake. To obtain weight loss, the recommended energy intake can be slightly less than the sum of the basal rate energy and the activity energy burned as measured by activity tracking device 20.

The inventors have realized that users do not like to track energy for the foods eaten, while users do like to track energy expended during physical activity, as evident by the popularity of activity tracking devices. The energy balancing system is designed to cater to this human desire to track good things (energy burned) and ignore bad things (energy eaten). Users track physical activity energy using activity tracking device 20, which gives positive feedback to encourage more physical activity, but do not have to track food energy. Instead, the energy balancer program determines how many kilojoules the user should eat, and then scales recipes to a scaled portion size that has the desired number of kilojoules. The user does not have to know how many kilojoules are in any of the foods eaten, because the energy balancer adjusts portion sizes using digital scale 62.

Figure 8:
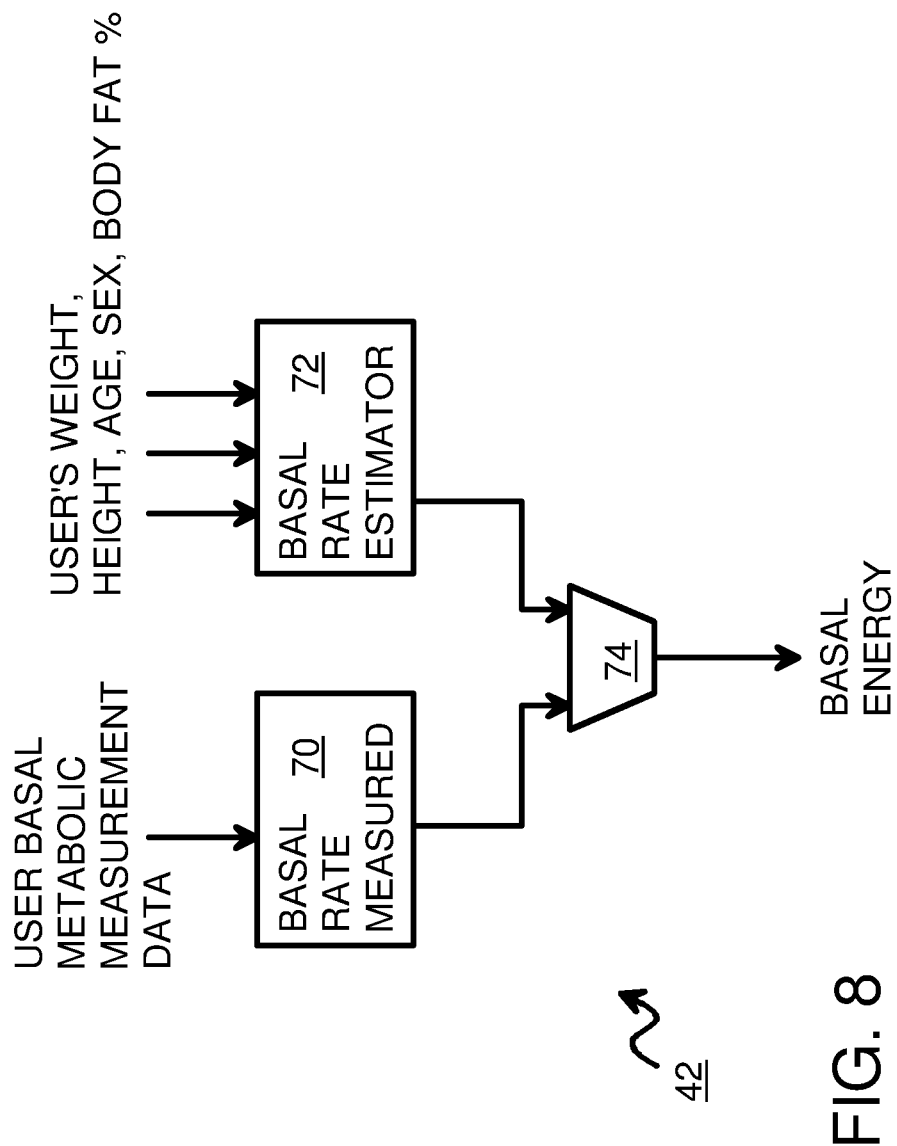
FIG. 8 shows the basal metabolic rate calculator in more detail.

FIG. 8 shows the basal metabolic rate calculator in more detail. Basal metabolic rate calculator 42 calculates basal rate 160 (FIG. 4). The user may have had their basal metabolic rate measured, such as by a metabolic cart in a laboratory setting. The flow rates of gases expired by a user are measured by a mask, as is the percentage amounts of Oxygen, Nitrogen, Carbon Dioxide, and Water Vapor. Such user basal metabolic data is input and converted to energy per day by measured basal rate checker 70. Data selector 74 then selects this measured basal rate as the basal energy per day that is then input to adder 44 (FIG. 7).

When no measured basal rate is available, then an estimate is made. Basal rate estimator 72 receives the user's weight, height, age, and sex, and calculates an estimate for the basal rate using an equation. Data selector 74 then selects this estimated basal rate as the basal energy per day that is then input to adder 44 (FIG. 7). The user can be prompted to enter their weight, height, age, and sex into mobile device 250 or another device that is providing the user an interface to the energy balancing program. This user-entered data can be stored by the memory unit 14 or storage devices 16 (FIGS. 5-6, 12-14).

The basal metabolic rate can be calculated by basal rate estimator 72 using the Harris-Benedict formula for basal metabolic rate that calculates basal metabolic rate as a function of height (h) in centimeters, weight (m) in kilograms, and age (a) in years of a male subject:

$$P_{men} = \left( \frac{13.7516 \text{ m}}{1 \text{ kilogram}} + \frac{5.0033 \text{ h}}{1 \text{ centimeter}} - \frac{6.7550a}{1 \text{ year}} + 66.4370 \right) \frac{\text{kilocalorie}}{\text{day}}$$

and for a female subject:

$$P_{women} = \left( \frac{9.5634 \text{ m}}{1 \text{ kilogram}} + \frac{1.8496 \text{ h}}{1 \text{ centimeter}} - \frac{4.6756a}{1 \text{ year}} + 655.0955 \right) \frac{\text{kilocalorie}}{\text{day}}$$

Figure 9:
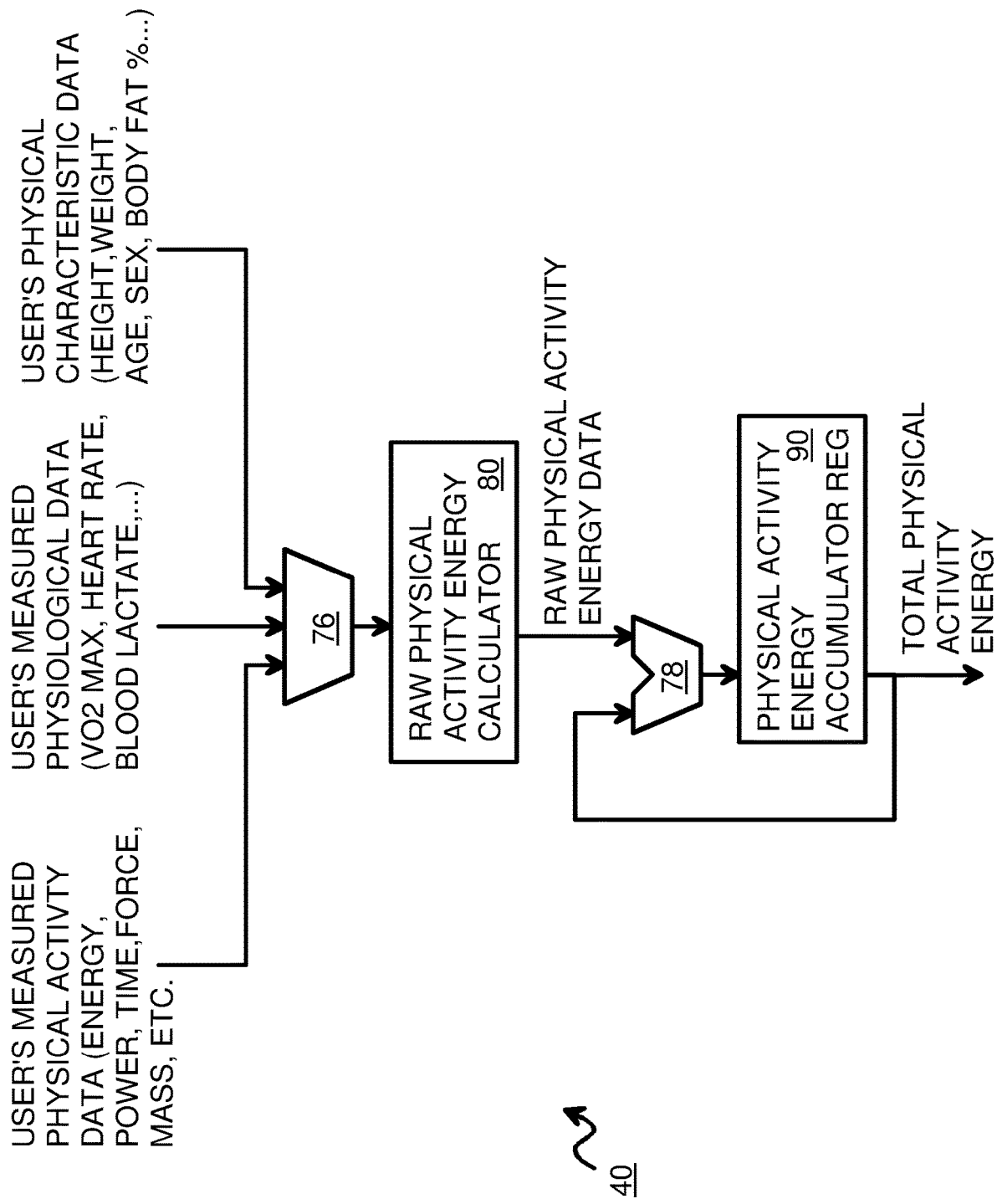
FIG. 9 is a diagram showing the physical activity energy calculator in more detail.

FIG. 9 is a diagram showing the physical activity energy calculator in more detail. Physical activity energy calculator 40 calculates the energy burned through physical activity such as physical activities 162, 164 (FIG. 4) that are tracked by activity tracking device 20. Physical activity energy calculator 40 can receive three types of data: measured physical activity data, measured physiological data, and physical characteristic data.

A first type of data is the user's measured physical activity data, such as measured by activity tracking device 20.

Physical activity energy calculator 40 calculates the energy burned through physical activity such as physical activities 162, 164 (FIG. 4) that are tracked by activity tracking device 20 (FIG. 5-6, 12-14) or tracked by GPS radio transceiver 24, gyroscopes 34, and accelerometers 32 of mobile device 250. This activity-tracking data can be in a variety of formats, such as a series of individually-transmitted data points or complete data files that are uploaded and stored in memory unit 14 or storage devices 16. The data can include a sequence of GPS, accelerometer, or gyroscope measurements. This user's measured physical activity data may include energy measurements, such as calories or kilojoules burned per unit time, which may be calculated by activity tracking device 20 from time and position data from GPS tracking. Power or torque generated by the user pedaling on a bike, mass of dumbbells or other weights lifted by the user, and force exerted on an exercise machine are other examples of user's measured physical activity data that is input to data selector 76.

Another type of data is physiological, which can be obtained using various sensors attached to a person who is exercising. This measured physiological data of the user can include VO2 max, heart rate, and blood lactate levels. This physiological data can be more personal and accurate than obtained from activity tracking device 20 because it is derived from actual measurements of the individual's physiological responses to activity. When using data from activity tracking device 20, physical activity energy calculator 40 may make some assumptions about the physiological response of the user to the activity, such as how many kilojoules a typical person burns each minute. This per time value can vary with the type of activity (running, jogging, or walking).

A third type of data is the user's physical characteristics data. The user inputs their weight, height, sex, and age, and perhaps their body fat percentage. Physical activity energy calculator 40 can use these physical characteristics along with other available data to estimate energy expenditure for various kinds of activities.

Data selector 76 selects one of the three data types for processing. When the first type of data is energy expenditure data, such as from activity tracking device 20, data selector 76 passes the energy data to raw physical activity energy calculator 80. The energy readings can be integrated over the time duration of the tracked activity to generate the raw activity energy data. The raw activity energy data from raw physical activity energy calculator 80 is then added by adder 78 to a running sum, and then stored in active energy accumulator register 90. Active energy accumulator register 90 stores and outputs the total active energy, which is also fed back to adder 78 so that subsequently processed activities can be accumulated into the total active energy.

When the first type of data is not formatted as energy expenditure data, raw physical activity energy calculator 80 converts the measured data into energy expenditure data. For example, GPS position data and time data can be used to generate a series of velocity values. The velocity data can then be used to calculate power for each GPS position and time data point. These data points are integrated or summed over time to get total energy.

When the second type of data is available for an activity, data selector 76 selects the second data for processing by raw physical activity energy calculator 80. The raw physiological data can be converted to energy expenditure for the activity by raw physical activity energy calculator 80 using various formulas or lookup tables.

When the third type of data is available for an activity, the activity type and duration may be entered manually by the user rather than tracked using activity tracking device 20. The user's activity tracking device 20 may have failed while the user was exercising, so the user has to manually enter the activity. The activity type, duration, along with the user's physical characteristics such as weight can be input into a formula or lookup table to estimate the energy expenditure.

For each reported activity in the day being energy balanced, data selector 76 selects the data types, and raw physical activity energy calculator 80 converts the raw data into energy expended during the activity. Adder 78 and active energy accumulator register 90 then accumulate the energy for all activities for that day. Once all reported activities have been obtained and processed, the final value from active energy accumulator register 90 is the total activity energy.

Figure 10:
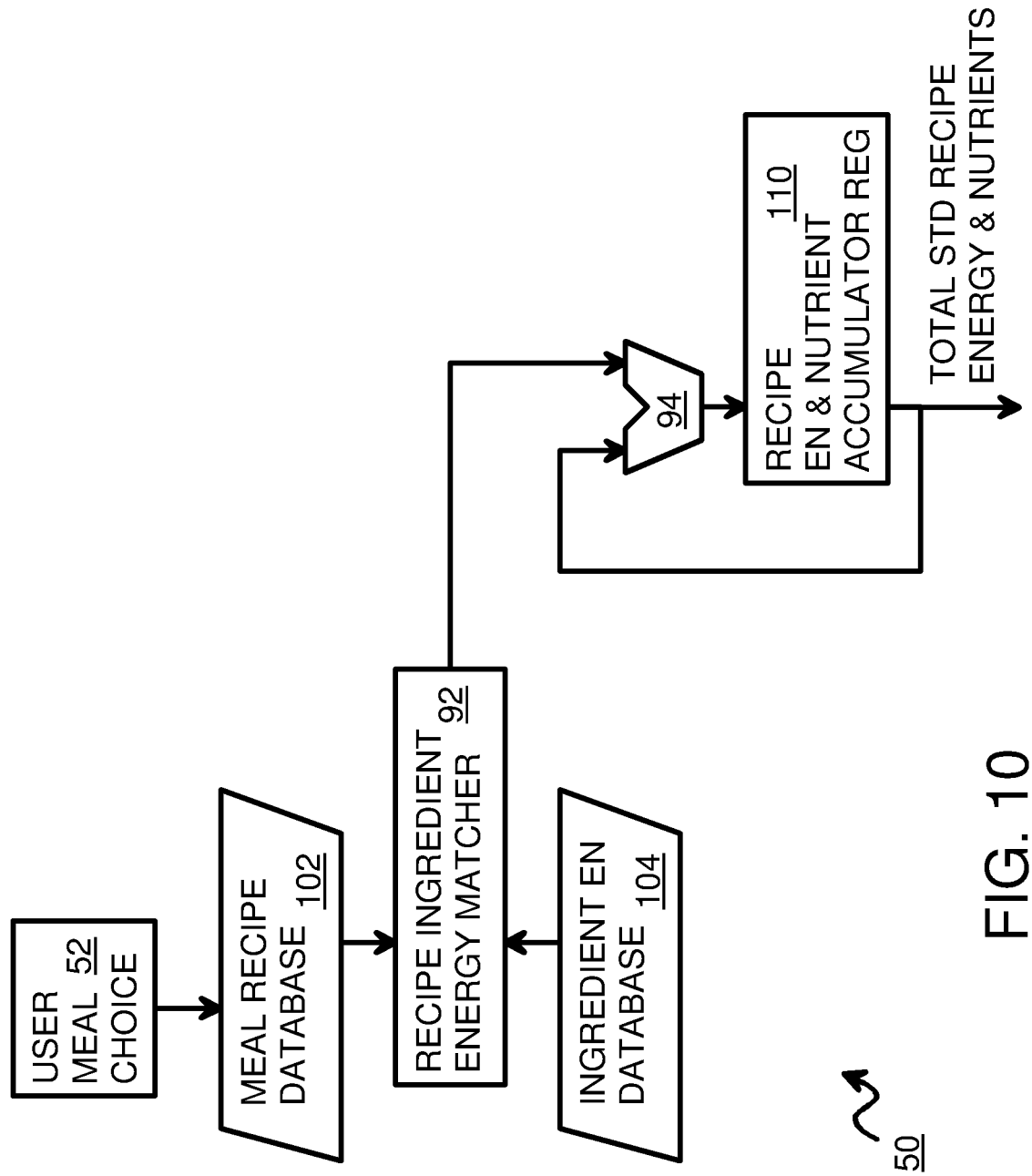
FIG. 10 shows the recipe energy and nutrient calculator in more detail.

FIG. 10 shows the recipe energy and nutrient calculator in more detail. User meal choice interface 52 accepts the user's choice of a set of M meals over some time period such as one day or one week. Each meal choice is looked up in meal recipe database 102 to find a corresponding data record that contains a set of ingredient food items in the meal, along with a recipe for combining the food items to form the meal. The recipe can include detailed weight, volume, or quantity values for the amount of each food item or ingredient to include in the recipe for the meal. The resulting match can be stored in memory unit 14 or in storage devices 16.

Each of these ingredients are looked up in ingredient energy database 104 to find a corresponding data record that contains the caloric energy density for that ingredient. The caloric energy density can be a number of kilojoules for a specific weight, volume, or quantity of that food ingredient. Nutrient density information for that food ingredient may also be located in ingredient energy database 104 or in other databases, such as data measured by a food nutrition analysis lab. Much of the energy and nutrient density information for common ingredients is publicly available.

Recipe ingredient energy matcher 92 multiplies the energy density for an ingredient by the amount of that ingredient in the recipe. This is for a standard portion or amount of the recipe that will be optimized and scaled later. For each nutrient, the nutrient density is multiplied by the amount of the ingredient. The resulting amount of energy and nutrients for that ingredient are formed into data records that are stored in memory unit 14 or in storage devices 16. These data records include the energy and nutrient amounts for that ingredient using the standard portions for the meal recipe.

The energy amount for each ingredient in the recipe is applied to adder 94 for accumulation by recipe energy and nutrient accumulator register 110. Once energy amounts for all ingredients have been accumulated, recipe energy and nutrient accumulator register 110 outputs the total energy for the meal. Likewise, for each nutrient, each ingredient's amount of that nutrient is successively accumulated into recipe energy and nutrient accumulator register 110. For N nutrients, N total nutrient amounts are output from recipe energy and nutrient accumulator register 110. This process can then be repeated for other meals chosen with user meal choice interface 52. The total energy and nutrient amounts for each meal can then be stored into memory unit 14 or storage devices 16. These values are for standard portions of the meals.

Figure 11:
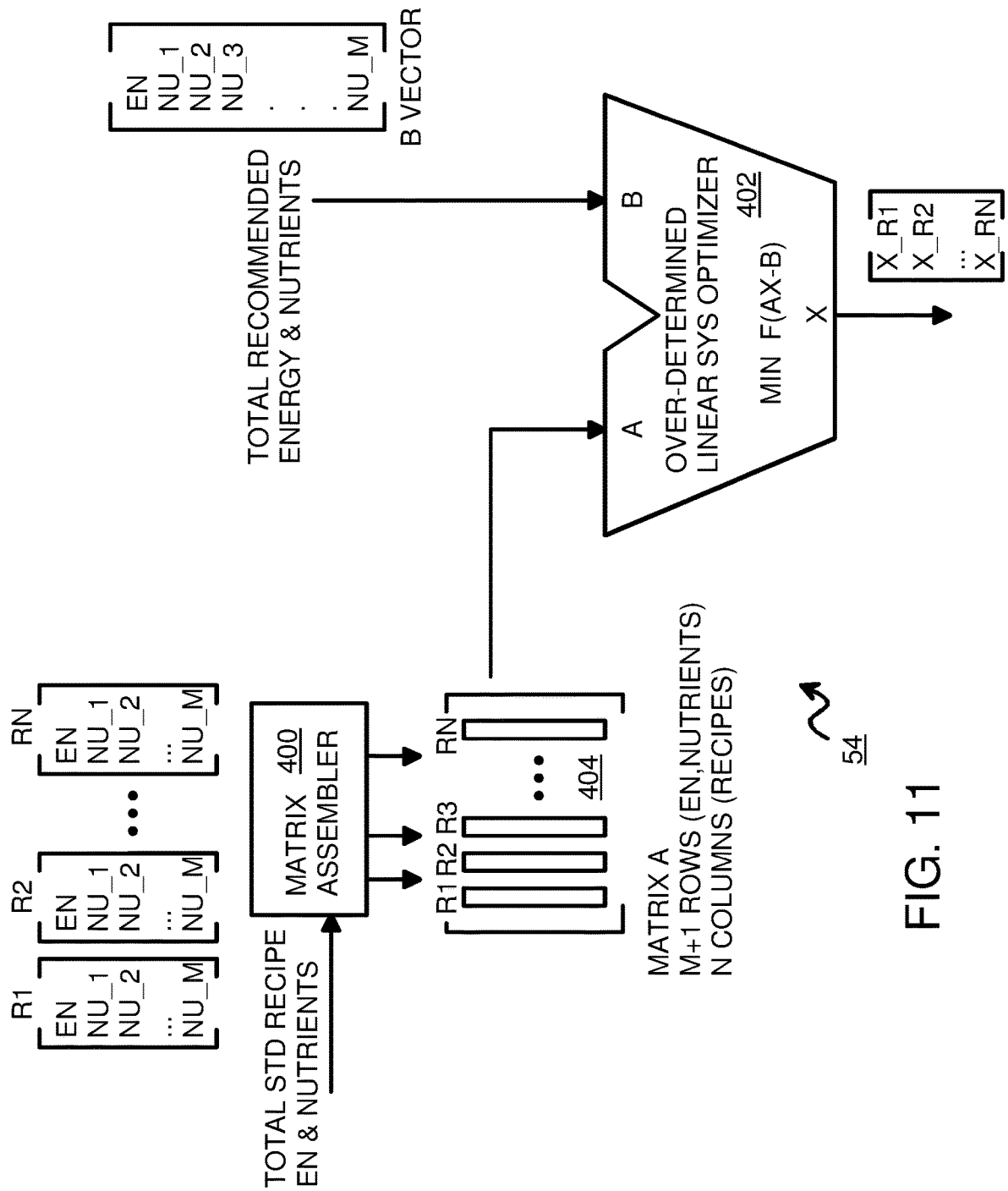
FIG. 11 shows the recipe portion-size optimizer in more detail.

FIG. 11 shows the recipe portion-size optimizer in more detail. Recipe portion-size optimizer 54 receives the total energy and nutrient amounts for each meal from recipe energy and nutrient calculator 50 (FIG. 7). These are for standard portions of the meals or recipes, so they are the total standard recipe energy and nutrient amounts. For each recipe of a selected meal, the total energy (kilojoules), and the total nutrients, for a standard portion, are arranged into a column by matrix assembler 400. The first column in matrix 404 has the energy EN, and nutrient amounts NU_1, NU_2, . . . NU_M for M nutrients for a standard portion of first recipe R1. The second column in matrix 404 has the energy EN, and nutrient amounts NU_1, NU_2, . . . NU_M for the M nutrients for a standard portion of second recipe R2, with the next columns being similarly arranged for subsequent recipes R3, R4, . . . RN, for N recipes.

The first row in matrix 404 has all the energy values EN for standard portions of all the N recipes. The second row has the nutrient values for the first nutrient NU_1 for all recipes. Subsequent rows have nutrient values for other nutrients.

Recipe portion-size optimizer 54 also receives the total recommended energy and nutrients from recommended food energy and nutrient intake calculator 46 (FIG. 7). This is the actual amount of kilojoules expended by the user, scaled up or down for weight gain or loss goals. The recommended kilojoules and nutrients are arranged into a vector with energy EN, and nutrient amounts NU_1, NU_2, . . . NU_M for M nutrients. These recommended values form the b vector that is applied to the B input of over-determined linear system optimizer 402. Matrix 404 is the A matrix that is applied to the A input of over-determined linear system optimizer 402.

The output of over-determined linear system optimizer 402 is scaling vector x, which has the scaling factors for each of the N recipes, X_R1, X_R2, X_R3, . . . X_RN. Each of the ingredients in first recipe R1 is multiplied by first scaling factor X_R1, while each ingredient in second recipe R2 is multiplied by second scaling factor X_R2, etc.

The standard amounts of each ingredient in a recipe is multiplied by that recipe's scaling factor to obtain the amount of the ingredient to be weighed by digital scale 62. When multiple portions are to be prepared, such as a 4-portion meal, the amount can be further multiplied by the number of portions to prepare. The other 3 portions can be given to other persons or saved for another day.

Matrix A and the b vector form an over-determined linear system that has multiple solutions of scaling vector x. A merit function can be evaluated and minimized to find a good value of scaling vector x to output. For example, the merit function that takes (Ax-b) as its input can be used to evaluate the current value of the scaling vector.

Over-determined linear system optimizer 402 multiplies matrix 404 (A) by scaling vector X (x) and compares it to the B vector (b) of the recommended values using a merit function to minimize the difference Ax-b. This is the difference between the desired b vector and the result of matrix A multiplied with the solution vector x. A solution could be found by testing different values of vector x and iterating to obtain a minimum value of the merit function, or various algorithms may be used, such as least-squares via QR decomposition. GPU 12 may be used to quickly perform such matrix operations, since graphics systems often use the matrix-processing capabilities of graphics processors.

Figure 12:
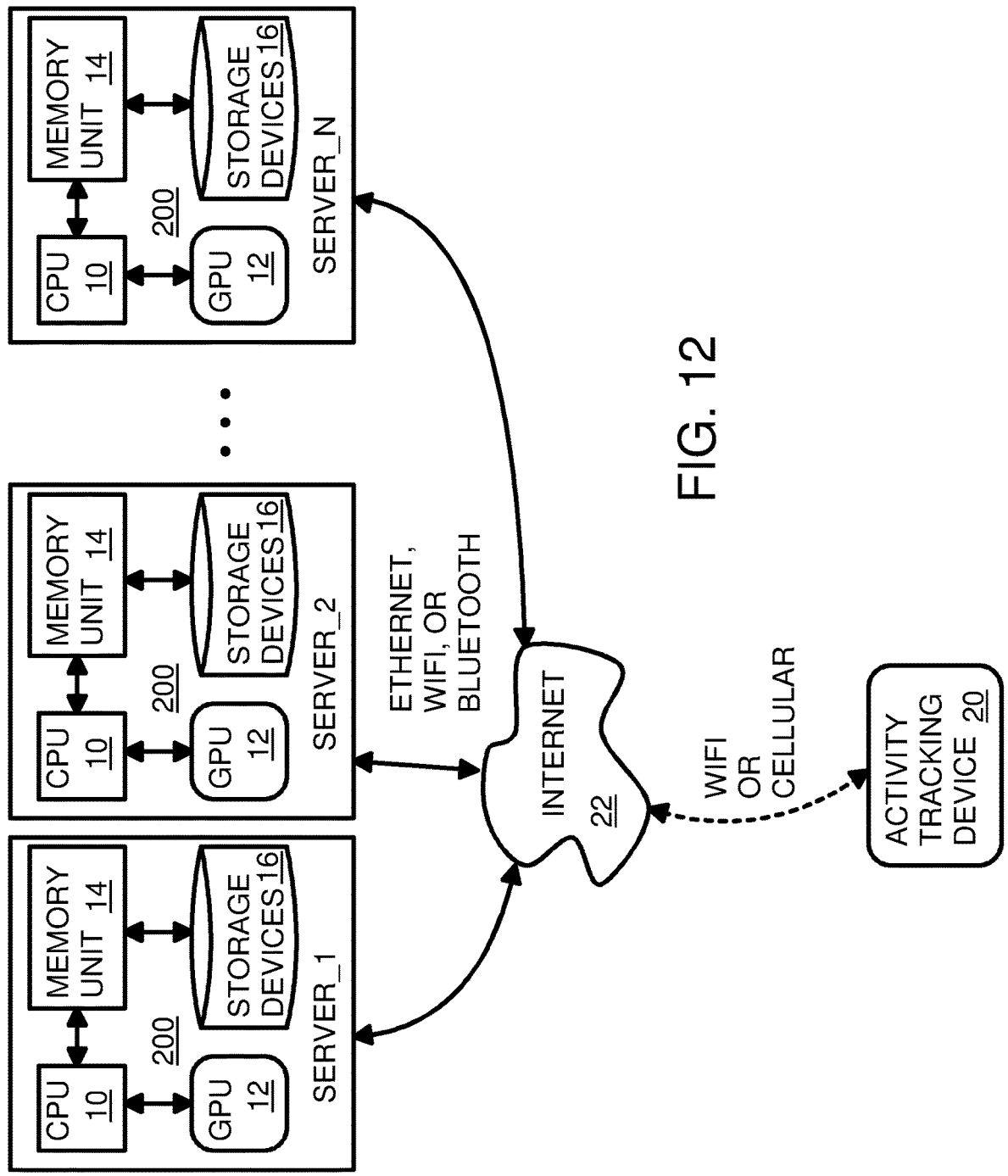
FIG. 12 shows a cloud server-based computing system that reads energy expenditure from a fitness-tracking device.

FIG. 12 shows a cloud server-based computing system that reads energy expenditure from a fitness-tracking device and measures food with a digital scale. Rather than have a single server 200, there are multiple instances of servers 200 that operate together as a cloud server. Data in storage devices 16 may be shared among the nodes of servers 200. Multiple users may simultaneously perform energy balancing and other operations by being assigned to different ones of servers 200, or for different time periods. CPU 10 in server 200 may be a multi-processor that supports multi-threading, allowing each server 200 to process many user requests at the same time. Data from a user's activity tracking device 20 can be uploaded to one over servers 200 and its data stored in storage devices 16 or in a shared database (not shown) that is available to all nodes. Many users may have many digital scales 62 (not shown) that can be controlled by any of servers 200. Servers 200 may be physically located at different geographic locations and may be shared with other web applications.

Figure 13:
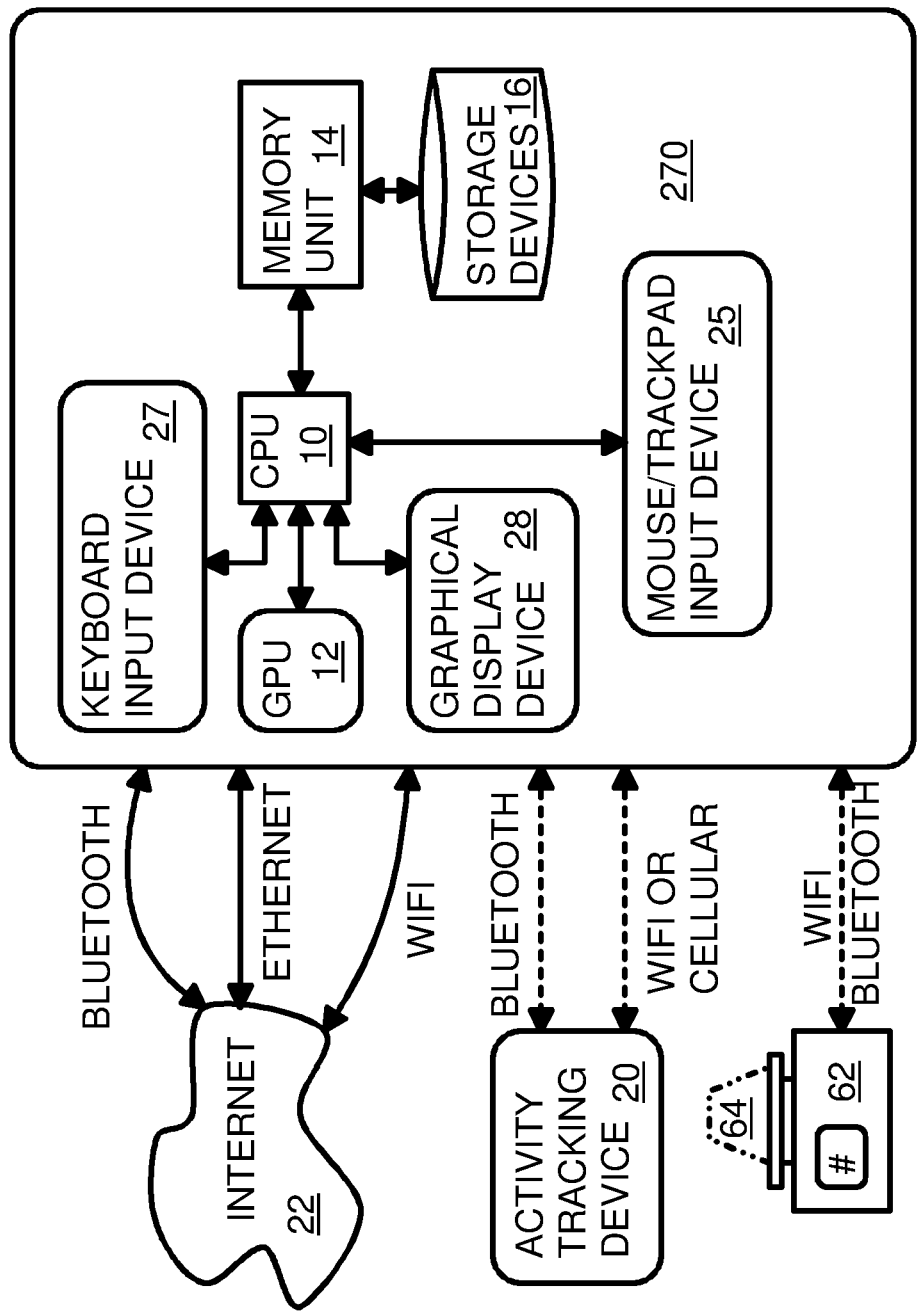
FIG. 13 shows a desktop computer that reads energy expenditure from a fitness-tracking device.

FIG. 13 shows a desktop computer that reads energy expenditure from a fitness-tracking device and measures food with a digital scale. Desktop computer 270 can be a desktop, laptop, or notebook Personal Computer (PC) that connects to Internet 22. Desktop computer 270 can pair with activity tracking device 20 using a protocol such as the WI-FI® protocol of the Wi-Fi Alliance of Austin, Tex. or the BLUETOOTH® protocol of the Bluetooth SIG of Kirkland, Wash., utilizing a cellular data network, or other wireless connection. The user can select meals and enter data using keyboard input device 27 or mouse or trackpad input device 25. Instructions and recipes may be displayed to the user on graphical display device 28. Digital scale 62 can also pair with desktop computer 270 using a protocol such as the WI-FI® protocol of the Wi-Fi Alliance of Austin, Tex. or the BLUETOOTH® protocol of the Bluetooth SIG of Kirkland, Wash.

Figure 14:
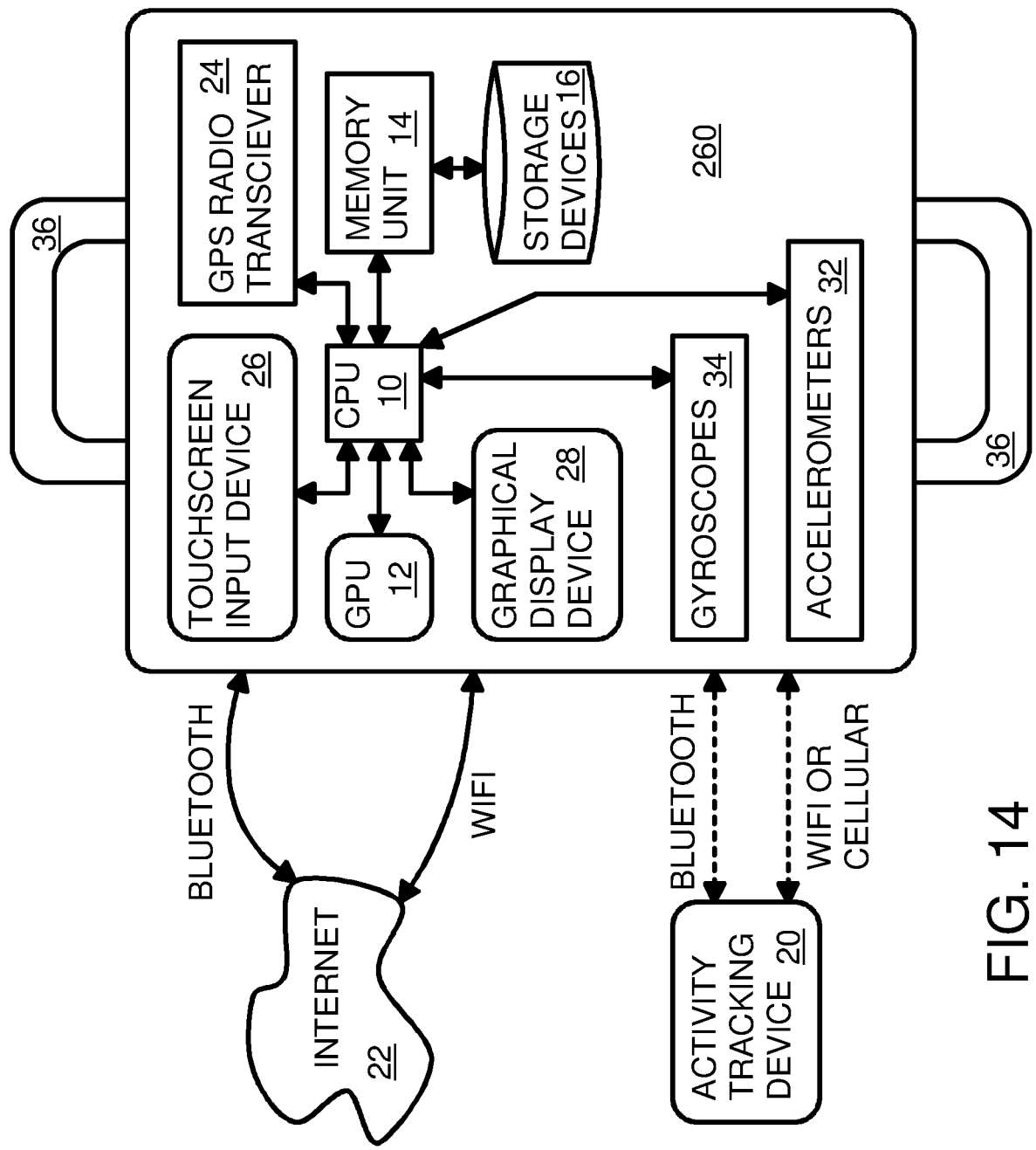
FIG. 14 shows a wearable computer that reads energy expenditure from a fitness-tracking device.

FIG. 14 shows a wearable computer that reads energy expenditure from a fitness-tracking device and measures food with a digital scale. Wearable device 260 has mount or strap 36 that allows it to be attached to person, such as the person's wrist or as a chest strap. Activity data from activity tracking device 20 can be received utilizing a protocol such as the WI-FI® protocol of the Wi-Fi Alliance of Austin, Tex. or the BLUETOOTH® protocol of the Bluetooth SIG of Kirkland, Wash., or utilizing a cellular data network. External databases and servers used by the energy balancing program can be accessed over Internet 22 utilizing a protocol such as the WI-FI® protocol of the Wi-Fi Alliance of Austin, Tex. or the BLUETOOTH® protocol of the Bluetooth SIG of Kirkland, Wash. Activity data can also be created by wearable device 260 without the use of activity tracking device 20 by CPU 10 executing an activity-tracking routine that obtains GPS data from GPS radio transceiver 24 that can be interpolated or adjusted by accelerometers 32 and gyroscopes 34. The user can make meal selections using touch screen input device 26. Referring also to FIG. 13, when wearable device 260 is paired with digital scale 62 (not shown), graphical display device 28 can instruct the user to add more of an ingredient to digital scale 62 until the calculated amount is reached.

ALTERNATE EMBODIMENTS

Several other embodiments are contemplated by the inventors. For example, a time period of 24 hours or one day has been described for performing the energy balance. However, some processing could occur throughout the day. Raw physical activity energy calculator 80 could process each activity as it is reported and accumulate its energy expenditure into active energy accumulator register 90 and then wait for the next activity. Alternately, activity data could be held until the end of the day and then all activities are processed by raw physical activity energy calculator 80.

Recipe portion-size optimizer 54 may optimize meals once per day or as each meal selection is made or updated by the user. The user could also select meals for a whole week, and then recipe portion-size optimizer 54 selects from these meals and optimizes for each day, or for the whole week. Meal portions that were previously optimized by recipe portion-size optimizer 54 could be updated as new activity is reported and processed by physical activity energy calculator 40.

A longer period than one day could be used, such as one week, or some components could use longer periods and other components use shorter periods. The energy balance could be performed each day and then again over a one-week period. The energy balance could be performed or updated multiple times per day, such as after each meal or physical activity. Nutrients could be balanced over a longer one-week period while energy are balanced on a 24-hour period. Meal choices could be made for several days or weeks at a time and stored, with daily meal choices being selected by the program from the user's earlier selections. Meals that were not selected by the user could be mixed in with user-selected meals, especially to improve nutrition. Substitutions generated by the program could be gradually introduced into the meal plans with gradually decreasing amounts provided over time. This allows the user's diet to gradually be improved by the energy balancing program, even when the user makes poor meal choices. If the user "cheats" and consumes too many kilojoules in a day, the energy balancing program could carry over the excess kilojoules consumed to the next day and reduce food portions the following days.

Recipe portion-size optimizer 54 can find a minimum of the merit functions of the energy and nutrient equations, to the limits of mathematical precision for the processor used for the optimization, or may stop processing after an acceptable minima is found, such as when the change in energy from a later iteration is within 1% of the minima from the current iteration, or after 5 iterations with changes to the minima of less than 5%.

While an optimization technique that minimizes the value output from the merit function has been described, different optimization approaches can accomplish the same goal by maximizing the value of an alternatively formulated merit function. For example, minimizing the value of a 2-norm merit function using least squares is mathematically equivalent to maximizing a gaussian probability distribution function using maximum likelihood techniques. Thus, maximizing the value output from one merit function may be equivalent to minimizing the value output from a different merit function. Minimizing the energy difference can occur by either maximizing a merit function or minimizing a merit function.

The ingredient ratios for a recipe may be exact or may have a range, such as to allow more or less of certain ingredients while still preparing the chosen meal. This can allow the energy balancer program to adjust recipes, such as to improve nutrition or to reduce energy density.

The standard portion size or standard amount for a meal could be the same as one portion, or the standard amount of the recipe could be for 2 or more portions. The user could use digital scale 62 to weigh the standard amount that is 2 portions, then cook the recipe and divide it into 2 before eating one portion, while saving the other portion for later. The energy balancing program could instruct the user to re-heat the second portion on a later date without requiring the user to cook the meal again. Thus multiple meals may be prepared at once and saved for later. The energy balancer may also have the user weight and cook one or more standard portions that are scaled. The recipe may call for a standard portion, while the user prepares one or more scaled portions while eating only one scaled portion at a time.

The standard portion size may differ for each recipe. The energy balancing program accounts for the different standard portion sizes since it optimizes the recipes for the total energy needed by the user, and adjusts recipe scaling factors as need to obtain the appropriate energy. Some recipes with large standard portions may have a small recipe scaling factor such as 0.2, while other recipes with small standard portions may have a recipe scaling factor such as 0.8, or even 1.3 for a very small standard portion. Thus there is no need to use a standard portion size that is the same size, such as 400 energy, or 10 ounces, etc. It is only important that each recipe has a standard portion size that later can be scaled by recipe portion-size optimizer 54.

The scaling factors could be the physical amount of a food item when the standard portion is set to one unit of the food item. The unit could be a slice (of pizza) or 100 grams, or 1 gram, 1 liter, 1 ml, etc. The units for the scaling factors can be arbitrary. The scaling factors could be a percent of the standard portion size. The unit of measure for the energy values $E1, E2, E3, \ldots En$ can be different or the same, and some can refer to grams, others to liters, and others to slices, whole bananas, etc.

For a recipe for a slice of lasagna, with a given energy E, and mass m, ×1 can be in units of slices of lasagna made using the recipe. Dividing Energy by mass, E/m, then ×1 is in units of grams of lasagna. For a smoothie or drink, which more naturally might be measured in volume, E/V, then ×1 is in liters (or milliliters) of the drink. Some recipes, or even complete meals, might have additional constraints, such as upper and lower bound values for the scaling factors x to ensure the recipe's integrity.

Over-determined linear system optimizer 402 may optimize by minimizing the 2-norm, using techniques such as QR decomposition with back substitution, conjugate gradient descent, or simulated annealing. Optimization of the 1-norm, or infinity-norm could also be performed using other techniques. Brute-force techniques of testing values of X and iterating could also be used. The merit function could apply different weights to the energy and nutrients, so that errors in the first row of matrix A for energy is weighted more than are errors in the other rows for nutrients. Alternatively, certain nutrients could be given higher weightings, such as to adjust a diet for vitamin D deficiency. The merit function could also require different values of X to fall within different ranges for maximum and minimum values. Recipe portion-size optimizer 54 may also simply optimize for energy and place little or no weight on nutrients.

The user's weight and height could be used to calculate their Body Mass Index (BMI), and when the BMI is above 25, the energy balancing program could automatically set a weight loss goal. Medical guidelines could be used to implement goals and to determine safe levels of weight loss goals. A weight-gain goal could be set for BMI below 20. Nutrient intake goals could also be set based on a doctor's advice. Alternatively, different metrics of obesity such as Corpuscular Index (CI), or the ratio of their waist diameter to their height may be used to automatically set a weight-loss goal.

While digital scale 62 has been described to measure the weight or mass of food 64, other kinds of food measurement devices could be substituted or combined, such as a liquid dispenser or flow meter with a fixed flow rate, where the volume of liquid dispensed is the flow rate multiplied by the dispense time. Because mass and volume are related by density, mass measurements may be converted to volume measurements for food items with known densities. The mass of food items may thus be measured by being converted to an equivalent volume (mass divided by the density) and then using volume measurement devices such as measuring cups, graduated cylinders, or pipettes may be used. Digital scale 62 may be a weight scale that measures the mass or weight of the food item, or digital scale 62 may be a volume scale that measures the volume of the food item.

Rather than measure raw ingredients for a recipe, a larger meal could be prepared with a fixed or pre-planned recipe, and then the serving portion weighed on digital scale 62 as food 64. The larger meal could be frozen, refrigerated, or stored for later use, and the user could measure out a different amount of the stored meal each day, depending on the energy needs for that day as determined by the energy balancing program. Likewise, a large batch of a smoothie could be made and stored, and then measured out by digital scale 62 for each meal. Pre-weighed ingredients of food items could be pre-packaged and used without digital scale 62, and restaurant meals could be inputted by the user and matched to a restaurant food database to indicate the energy and nutrients ingested. Then other at-home meals could be adjusted and weighed by digital scale 62 to compensate for the restaurant food. Leftover restaurant food or other premade meal components could be weighed by digital scale 62 to a target portion calculated by the energy-balancing program when consumed at home.

Some ingredients may not be measured on digital scale 62, such as for pre-defined food ingredients, such as a medium egg, a pinch of salt, or liquid measurements such as ¾ of a cup of milk. A recipe may have a combination of measured and non-measured ingredients. Certain food ingredients may not be scaled with other ingredients. For example, the recipe portion-size optimizer 54 may scale the amount of flour, baking soda, raisins, and milk for a recipe, but not scale the one medium egg in that same recipe.

Mobile device 250 or a local PC or other device could pair with digital scale 62 utilizing a protocol such as the WI-FI® protocol of the Wi-Fi Alliance of Austin, Tex. or the BLUETOOTH® protocol of the Bluetooth SIG of Kirkland, Wash. Mobile device 250 could execute a weighing program or sub-routine of the energy balancing program, and display meal choices to the user on the display of mobile device 250, allowing the user to select preferred meals. Then the energy balancing program can optimize the meal recipe for the target energy and nutrients, and then display instructions to the user to weigh each food item on digital scale 62, and verify that the correct weights are measured.

The weights of food that the user measures using digital scale 62 could be approximate, such as accurate within 5%, 10%, or 20%, and the exact weight measurement fed back to the energy balancing program for use in adjusting the next meal, or other ingredients in the current meal. Energy targets could thus be approximate and yet still be compensated for over and under measurements over several meals. Matching can be to within some range, such as within 5%.

Digital scale 62 or food-portion measurement controller 60 can be used to prompt the user to weigh the food item or ingredient until the calculated weight is reached. Alternately, the user can use an app on a mobile device to perform weighing, such as an app for digital scale 62. The energy balancing program can also physically display instructions generated by food-portion measurement controller 60 on the user's mobile device 250 or on another device.

In one embodiment, food-portion measurement controller 60 may instruct the user to place an empty mixing bowl on digital scale 62, then food-portion measurement controller 60 reads digital scale 62 for the weight of the empty bowl. Next food-portion measurement controller 60 can instruct the user to add more of the first ingredient. As the use slowly adds the first ingredient, digital scale 62 sends the current weight to food-portion measurement controller 60. When the added weight nears the weight of the scaled portion of the first ingredient, food-portion measurement controller 60 sends a display message to the user that the target is near and to add more slowly. The user slowly adds more of the first ingredient until the target weight is reached by digital scale 62, and food-portion measurement controller 60 can send an audible or visual message to the user to stop adding the first ingredient. If too much of the first ingredient was added, food-portion measurement controller 60 can instruct the user to remove some of the ingredient. The target weight is the weight of the empty bowl plus the scaled weight of the first ingredient. Then food-portion measurement controller 60 can instruct the user to add the second ingredient, with the target weight from digital scale 62 being the weight of the empty bowl, plus the scaled-portion weight of the first ingredient, plus the scaled-portion weight of the second ingredient. Other ingredients may be added in a similar fashion using the same mixing bowl. Of course, ingredient may also be weighed one at a time and mixed after all weighing is completed.

Mobile device 250, or server 200, or another computing device stores and executes a software program that converts the weights, quantities, or volumes of each food item in the new meal recipes into a computer-readable format that can be transmitted electronically via a direct connection, or via the internet, to the measuring and dispensing device such as digital scale 62 that is capable of measuring or dispensing precise weights, volumes, or quantities to match the weights, quantities, or volumes of each food item in the scaled meal recipe. Liquid measures may be converted to weights or may be approximated as weights.

Various equations may be used by basal rate estimator 72 to generate the estimate of the basal rate. For example, the Harris-Benedict formula revised by Roza-Shizgal may be used for a male user:

$$P_{men} = \left(\frac{13.397 \text{ m}}{1 \text{ kilogram}} + \frac{4.799 \text{ h}}{1 \text{ centimeter}} - \frac{5.677a}{1 \text{ year}} + 88.362\right)\frac{\text{kilocalorie}}{\text{day}}$$

or for a female subject:

$$P_{women} = \left(\frac{9.247 \text{ m}}{1 \text{ kilogram}} + \frac{3.098 \text{ h}}{1 \text{ centimeter}} - \frac{4.330a}{1 \text{ year}} + 447.593\right)\frac{\text{kilocalorie}}{\text{day}}$$

Basal rate estimator 72 may use the Mifflin-St. Jeor formula for basal metabolic rate that calculates basal metabolic rate as a function of height (h) in centimeters, weight (m) in kilograms, and age (a) in years with the constant S=5 for men and S=−161 for women:

$$P = \left(\frac{10.0 \text{ m}}{1 \text{ kilogram}} + \frac{6.25 \text{ h}}{1 \text{ centimeter}} - \frac{5a}{1 \text{ year}} + S\right)\frac{\text{kilocalorie}}{\text{day}}$$

Alternately, when the body fat percentage is available to basal rate estimator 72, the basal metabolic rate may be calculated by any statistical regression relationship that relates height, weight, age, sex, and body fat percentage to basal metabolic rate.

Wearable device 260 could have additional components, such as to measure temperature or heart rate, or could connect to physiological sensors to collect physiological data.

The measurements of daily physical activity and exercise may include one of the following measurements, and are subsequently stored in the computing device's memory or storage devices:

Energy produced by the user during a specific time period.

Power produced by the user at various measured points during a time period, along with the time difference between each power measurement.

The volumetric flow rate of Nitrogen, Oxygen, and Carbon Dioxide exhaled by the user at various measurement points during a time period, and the length of time between each measurement point.

The blood lactate level of the user at various measurement points during a time period, and the length of time between each measurement point.

The instantaneous heart rate of the user at various measurement points during a time period, and the times when each measurement was taken.

The torque the user applies to a bar or beam structure attached to a center pivot, the rotational velocity of the bar or beam structure attached to the central pivot, and the times when each measurement of torque and angular velocity was taken.

The force the user applies to a rope, chain, or cable, the linear velocity of the rope, chain, or cable, and the times when each measurement of force and velocity was taken.

The fundamental vibrational frequency of an object the user is applying a force to, the linear velocity and angular velocity of the object under the applied force from the user, and the times when each measurement of vibrational frequency and velocities was taken.

The acceleration of the user at various points during a time period measured by a set of three accelerometers attached to the user and oriented to measure acceleration in three orthogonal directions, along with the times when each set of measurements was taken. Data from accelerometers and gyroscopes can also provide activity data for activities that use only arm movements (weight lifting), or combine locomotion with arm movements (tennis for example).

The acceleration that the user imparts to an object of known mass at various points during a time period measured by a set of three accelerometers attached to the object of known mass and oriented to measure acceleration in three orthogonal directions, along with the times when each set of measurements was taken.

The angular acceleration of the user at various points during a time period measured by a set of three gyroscopes attached to the user and oriented to measure angular acceleration in three orthogonal directions, along with the times when each set of measurements was taken.

The angular acceleration that the user imparts to an object of known mass moment of inertia at various points during a time period measured by a set of three gyroscopes attached to the object of known mass moment of inertia and oriented to measure angular acceleration in three orthogonal directions, along with the times when each set of measurements was taken.

The latitude, longitude, and altitude of the user measured at various point during a time period, along with the times when each measurement was taken.

The velocity of the user, the properties of the physical media the user is moving through (water temperature, water salinity, and water velocity relative to the user for swimming; air temperature, air relative humidity, user elevation above sea level for running, walking, hiking, skiing, bicycling, and other motion based activities), and the gradient of the surface the user is moving along measured at various points during a time period, along with the times when each measurement was taken.

The change in body temperature of a user measured at various points during a time period and the ambient air temperature, along with the times when each measurement was taken.

The estimated user activity level selected by the user via a touch screen, or keyboard device attached to the computing device, from a list or set of activity levels.

The software program can determine the type of measurement data provided by identifying the sensor type of a directly-connected sensor in the case of streamed measurement data, by identifying the type of data from advertised metadata from a connected measurement device communicating with the BLUETOOTH® protocol of the Bluetooth SIG of Kirkland, Wash. or the ANT+™ protocol of ANT Wireless, a division of Garmin Canada, of Cochrane, Alberta, Canada, or by identifying the file extension or file header by matching it to a set of known file types when a complete data file is input. Once identified, the software program then converts the measurements of user activity into an energy value based on the type of data that is input, which is in turn stored in the computing device's memory or storage devices:

When energy measurement data is provided, it is passed directly through raw physical activity energy calculator 80 without conversion.

When power and time measurement data is provided, the energy value is computed as the sum of each power measurement multiplied by its corresponding time period of the measurement.

When the volumetric flow rate of Nitrogen, Oxygen, and Carbon Dioxide exhaled by the user and time measurement data is provided, the energy value is computed by first computing the Respiratory Exchange Ratio (RER) between Carbon Dioxide and Oxygen to determine the quantity of energy produced per liter of Oxygen consumed by the individual, then multiplying this energy value by the difference in the volume of Oxygen exhaled by the individual from the standard amount of Oxygen in a standard atmosphere.

When the blood lactate level measurement data is provided, the energy value is computed by summing the power value calculated using the user input measurement data for blood lactate levels and power to determine the power value corresponding to the measured blood lactate level multiplied by its corresponding time period of the measurement.

When the instantaneous heart rate measurement data is provided, the energy value is computed by summing the power value calculated using the user input measurement data for heart rate and power to determine the power value corresponding to the measured heart rate level multiplied by its corresponding time period of the measurement.

When the torque and angular velocity measurement data is provided, the energy value is computed as the sum of each torque measurement multiplied by both the angular velocity and the corresponding time period of the measurement.

When the force and velocity measurement data is provided, the energy value is computed as the sum of each force measurement multiplied by both the velocity and the corresponding time period of the measurement.

When the natural frequency and velocity measurement data is provided, the energy value is computed as the sum of each natural frequency measurement squared multiplied by a constant based on the shape and material of the object being measured, the velocity of the object, and the corresponding time period of the measurement.

When the acceleration and user mass measurement data is provided, the energy value is computed as the sum of the magnitude of each acceleration measurement multiplied by both the mass of the user and the corresponding time period of the measurement.

When the acceleration and object mass measurement data is provided, the energy value is computed as the sum of the magnitude of each acceleration measurement multiplied by both the mass of the object and the corresponding time period of the measurement.

When the angular acceleration and user mass moment of inertia measurement data is provided, the energy value is computed as the sum of the magnitude of each angular acceleration measurement multiplied by both the mass moment of inertia of the user and the corresponding time period of the measurement.

When the angular acceleration and object mass moment of inertia measurement data is provided, the energy value is computed as the sum of the magnitude of each angular acceleration measurement multiplied by both the mass moment of inertia of the object and the corresponding time period of the measurement.

When the latitude, longitude, and altitude measurement data for the user activity is provided, the energy value is computed by summing the kinetic energy value computed by first determining the surface area of the user as a function the height and mass of the user, then calculating the air density as a function of the altitude of the user, finding the surface gradient by dividing the change in altitude by the change in position data between successive measurements, and then multiplying the time period between successive measurements by a term for the power required to overcome aerodynamic drag on the user summed with a term for the power required to overcome gravitational drag on the user. The term for the power required to overcome aerodynamic drag is computed by taking one half of the air density computed from the altitude multiplied by an estimate of the user drag coefficient determined from a relationship based on the user surface area times the cube of the user velocity. The amount of power required to overcome gravitational force is calculated by multiplying the mass of the user by the velocity of the user and multiplying that term by the constant of gravitational acceleration measured on the Earth's surface times the sine function of the arc tangent function of the gradient of the surface the user is moving across.

When the velocity measurement data for the user activity is provided, the energy value is computed by summing the kinetic energy value computed by first determining the surface area of the user as a function the height and mass of the user, then multiplying the time period between successive measurements by a term for the power required to overcome aerodynamic drag on the user summed with a term for the power required to overcome the gravitational drag on the user. The term for the power required to overcome aerodynamic drag is computed by taking one half of the air density computed from altitude multiplied by an estimate of the user drag coefficient determined from a relationship based on the user surface area times the cube of the user velocity. The term for the power required to overcome gravitational force is calculated by multiplying the mass of the user by the velocity of the user and then multiplying that term by the constant of gravitational acceleration measured on the Earth's surface times the sine function of the arc tangent function of the gradient of the surface the user is moving across.

When the user body surface temperature and ambient air temperature measurement data for the user activity is provided, the energy value is computed by summing an energy term computed by multiplying the time period between successive measurements with a term comprised of the change in the user's body stored thermal energy summed with terms corresponding to the energy transferred from the user's body to the surrounding environment due to radiation and the energy transferred from the user's body to the surrounding environment due to convective thermal energy transfer. The term for the user's stored thermal energy is computed from the mass of the user multiplied by the specific heat of the user times the change in temperature of the user from the measurement divided by the time period of the measurement. The term for the energy transferred from the user due to radiation is calculated by multiplying the emissivity of the user by Boltzmann's constant by the surface area of the user computed from a relationship including the user's height and weight and the difference between the body temperature of the user to the fourth power and the environmental temperature to the fourth power. The term for the energy transferred from the user due to convection is found by multiplying a term proportional to the square root of the velocity of the user times the surface area of the user multiplied by the difference between the user body temperature and the ambient air temperature.

When the user estimated activity level is provided, the energy value is derived by matching the user estimated activity level, along with the user height, weight, age, and sex to a corresponding data record in a database stored either in memory or the storage device of the computing device that contains an activity energy value that corresponds to the user estimated activity level value, height, weight, age, and sex.

A program can divide the raw energy value ($E_k$) by an estimate of human biomechanics efficiency ($\varepsilon$) for the specific type of activity performed to determine a value for the energy expended (E) by the user during the activity measured, which is subsequently stored in its memory or storage devices.

Physical activity energy calculator 40, user meal choice interface 52, recipe portion-size optimizer 54, raw physical activity energy calculator 80, and other components may be implemented in a variety of technologies, using various combinations of software, hardware, firmware, routines, modules, functions, etc. Components may be geographically dispersed or may be integrated. Some or all components could be implemented in an Application-Specific Integrated Circuit (ASIC) or other hardware to increase processing speed and lower power consumption.

The background of the invention section may contain background information about the problem or environment of the invention rather than describe prior art by others. Thus inclusion of material in the background section is not an admission of prior art by the Applicant.

Any methods or processes described herein are machine-implemented or computer-implemented and are intended to be performed by machine, computer, or other device and are not intended to be performed solely by humans without such machine assistance. Tangible results generated may include weighing food items, reports or other machine-generated displays on display devices such as computer monitors, projection devices, audio-generating devices, and related media devices, and may include hardcopy printouts that are also machine-generated. Computer control of other machines is another tangible result. The program or various components may include instructions that are stored on non-transitory computer-readable media such as a hard disk, DRAM, SRAM, flash memory, or other memory devices.

Any advantages and benefits described may not apply to all embodiments of the invention. When the word "means" is recited in a claim element, Applicant intends for the claim element to fall under 35 USC Sect. 112, paragraph 6. Often a label of one or more words precedes the word "means". The word or words preceding the word "means" is a label intended to ease referencing of claim elements and is not intended to convey a structural limitation. Such means-plus-function claims are intended to cover not only the structures described herein for performing the function and their structural equivalents, but also equivalent structures. For example, although a nail and a screw have different structures, they are equivalent structures because they both perform the function of fastening. Claims that do not use the word "means" are not intended to fall under 35 USC Sect. 112, paragraph 6. Signals are typically electronic signals, but may be optical signals such as can be carried over a fiber optic line.

The foregoing description of the embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

We claim:

1. An energy balancing system for use by a user, comprising:
   at least one processor;
   at least one memory unit connected to said at least one processor;
   at least one storage device connected to said at least one memory unit, wherein said at least one storage device stores at least one stored recipe for a meal;
   at least one input device connected to said at least one processor, wherein at least one said input device receives information relating to energy expenditure from physical activity by the user across a period of time, wherein at least one said input device receives information relating to the basal metabolism of the user, and wherein at least one said input device includes a user meal choice interface for receiving at least one selection from the user of at least one said stored recipe for a meal;
   a recipe portion-size optimizer configured to run on said at least one processor, said recipe portion-size optimizer configured to receive from said at least one said input device said information relating to energy expenditure from physical activity by the user across a period of time and said information relating to the basal metabolism of the user, said recipe portion-size optimizer configured to utilize said information relating to energy expenditure from physical activity by the user across a period of time and said information relating to the basal metabolism of the user to adjust at least one said stored recipe to an optimized recipe by generating a plurality of recipe scaling factors, each said recipe scaling factor associated with a different ingredient of said stored recipe; and
   a food-portion measurement controller connected to said at least one processor, wherein said recipe portion-size optimizer is configured to control said food-portion measurement controller to control at least one characteristic of said optimized recipe by at least one of
      controlling a food measurement device to dispense a target amount of an ingredient; and
      instructing the user to add an amount of said ingredient, measuring the amount of said ingredient added, comparing the amount of said ingredient added against a target amount, instructing the user to add more of said ingredient when the target amount has not been reached, and instructing the user to remove an amount of said ingredient when the target amount has been exceeded.

2. The energy balancing system of claim 1, wherein at least one said input device comprises an activity tracking device; said activity tracking device comprising at least one of a sensor configured to monitor the heart rate of the user, an accelerometer configured to measure motion of the user, a gyroscope configured to measure user motion, and a GPS radio transceiver configured to determine at least one of the position, orientation, and velocity of the user.

3. The energy balancing system of claim 1, wherein at least one said input device comprises at least one of:
   an accelerometer connected to said processor; and
   a Global Positioning System radio transceiver for receiving Global Positioning System (GPS) data.

4. The energy balancing system of claim 1, wherein said food measurement device is at least one of
   a digital weight scale that includes a display;
   a digital volume scale that includes a display;
   a liquid dispenser; and
   a flow meter with a fixed flow rate.

5. The energy balancing system of claim 1, wherein said at least one input device is connected to said at least one processor wirelessly.

6. The energy balancing system of claim 1, wherein said food-portion measurement controller is connected to said at least one processor wirelessly.

7. A non-transitory computer-readable storage medium containing instructions that configure at least one processor that is in communication with at least one memory unit, at least one storage device connected to said at least one memory unit, at least one input device, and at least one digital scale, to perform balancing of energy expenditure by a user with food intake by the user by:
   storing, at the at least one storage device, at least one stored recipe that instructs the production of a food portion and an energy amount corresponding to said food portion, each said stored recipe having at least one ingredient;
   receiving, at the at least one processor, at least one said stored recipe;
   generating, at the at least one processor, a total recommended energy intake for the user;
   generating, at the at least one processor, a recipe scaling factor for each said stored recipe received at the at least one processor;
   optimizing each said stored recipe by multiplying, at the at least one processor, each said recipe scaling factor by said energy amount of each said stored recipe to obtain an optimized recipe having an optimized energy amount, wherein said optimized recipe minimizes an energy difference between said total recommended energy intake and said optimized energy amount of said recipe; and controlling, from the at least one processor, the digital scale to control at least one characteristic of said optimized recipe by instructing the user to add an ingredient to a workpiece on the digital scale, measuring the weight of said ingredient, instructing the user to stop adding said ingredient when a target weight of said ingredient is reached, and instructing the user to remove an amount of said ingredient when said target weight is exceeded.

8. The non-transitory computer-readable storage medium of claim 7; wherein said storing said at least one stored recipe further comprises storing at least a first nutrient amount; and further comprising:

generating, at the at least one processor, at least a first total recommended nutrient intake for a first nutrient; and optimizing said first nutrient amount by multiplying, at the at least one processor, each said recipe scaling factor by said first nutrient amount of each said stored recipe to obtain said optimized recipe having an optimized first nutrient amount, wherein said optimized recipe minimizes a first nutrient difference between said first total recommended nutrient intake and said optimized first nutrient amount of said optimized recipe.

9. The non-transitory computer-readable storage medium of claim 8;

wherein said optimizing further comprises generating, at said at least one processor, a first merit function that indicates how closely energy contained in a quantity of food produced by said optimized recipe matches the energy expenditure by the user;

wherein said optimizing further comprises generating, at said at least one processor, a second merit function that indicates how closely at least one nutrient in said optimized recipe matches a target range for said at least one nutrient; and wherein said optimizing further comprises a selected one of (a) minimizing, at said at least one processor, an output of said first merit function and an output of said second merit function, and (b) maximizing, at said at least one processor, an output of said first merit function and said second merit function.

10. The non-transitory computer-readable storage medium of claim 8, wherein said optimizing further comprises solving, at said at least one processor, an overdetermined linear system to minimize said energy difference and said first nutrient difference.

11. The non-transitory computer-readable storage medium of claim 8, further comprising:

receiving, at said at least one input device, a selection by the user of at least one said stored recipe;

assembling, at said at least one processor, a record for each said stored recipe into a column, said column comprising an energy row containing said energy amount for said stored portion of said stored recipe, and at least one additional row wherein each said row contains a nutrient amount associated with said stored portion;

arranging, at said at least one processor, said records for said stored recipes into columns to form a recipe energy and nutrients matrix;

assembling, at said at least one processor, said total recommended energy intake, and said first total recommended nutrient intake into a recommended-intake column, said recommended-intake column comprising an energy row containing said total recommended energy intake, and said recommended-intake column comprising a first nutrient row containing said total recommended first nutrient intake;

receiving, at said at least one processor, said recipe energy and nutrients matrix as a first input, and said recommended-intake column as a second input; and generating, at said at least one processor, said plurality of recipe scaling factors by minimizing a merit function that evaluates said recipe energy and nutrients matrix multiplied by said plurality of recipe scaling factors, minus said recommended-intake column.

12. The non-transitory computer-readable storage medium of claim 11, further comprising:

receiving, at said at least one processor, input comprising a merit function of the form Ax-b, wherein A is said recipe energy and nutrients matrix, x is a vector of said plurality of recipe scaling factors, and b is a vector of said recommended-intake column; and minimizing, at said at least one processor, an output of said merit function.

13. The non-transitory computer-readable storage medium of claim 7, further comprising receiving, at said at least one processor, from at least one said input device, input relating to activity by the user across a period of time; and calculating, at said at least one processor, a physical activity energy expenditure based on said input relating to activity by the user across said period of time;

generating, at said at least one processor, a basal metabolic rate for the user;

multiplying, at said at least one processor, said period of time by said basal metabolic rate to obtain a basal energy expenditure;

adding, at said at least one processor, said physical activity energy expenditure and said basal energy expenditure to obtain a total energy expenditure;

wherein said generating, at said at least one processor, of said total recommended energy intake for the user is based in part on said total energy expenditure.

14. The non-transitory computer-readable storage medium of claim 13, wherein said period of time is one day.

15. A non-transitory computer-readable storage medium that configures at least one processor, the at least one processor in communication with at least one input device, at least one output device including a digital scale, and at least one storage device, to perform:

storing, at the at least one storage device, at least one stored recipe having a stored portion and an energy amount corresponding to said stored portion, each said recipe having at least one ingredient;

receiving, at the at least one processor, at least one said stored recipe;

generating, at the at least one processor, a total recommended energy intake for the user;

generating, at the at least one processor, a recipe scaling factor for each said stored recipe received at said at least one processor;

optimizing each said recipe by multiplying, at the at least one processor, each said recipe scaling factor by said energy amount of each said stored recipe to obtain an optimized recipe having an optimized energy amount, wherein said optimized recipe minimizes an energy difference between said total recommended energy intake and said optimized energy amount of said optimized recipe; and controlling, from the at least one processor, the at least one output device by instructing the user to add an ingredient to the digital scale, measuring the weight of said ingredient, instructing the user to stop adding said ingredient when a target weight of said ingredient is reached, and instructing the user to remove an amount of said ingredient when said target weight is exceeded.

* * * * *